Figures 5A, 5B, 5C:
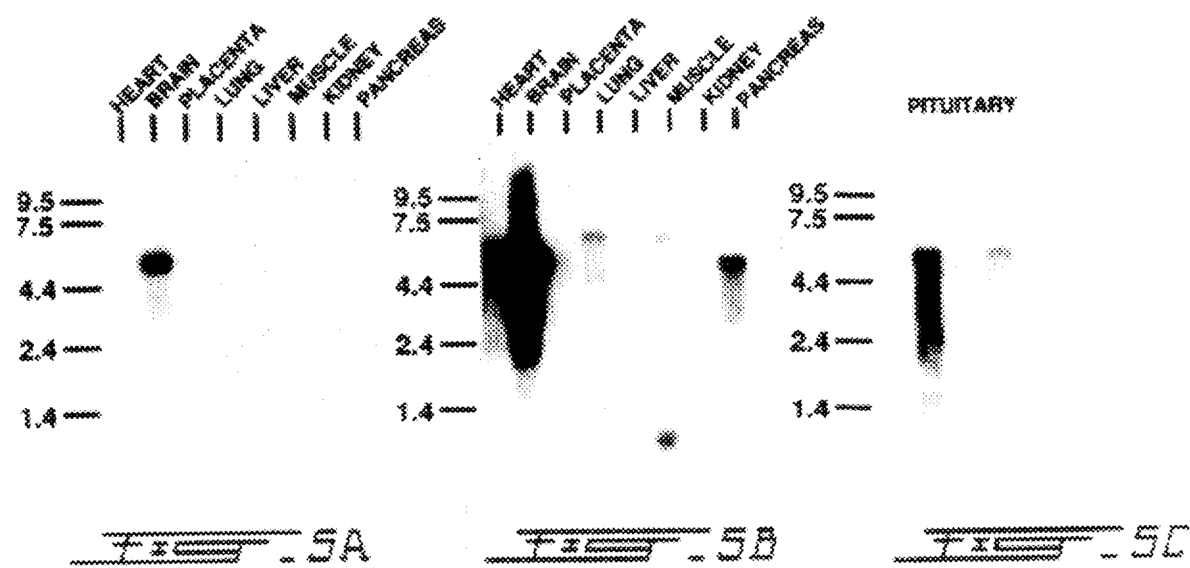

US005789564A

United States Patent [19]

Seidah et al.

[11] Patent Number: 5,789,564

[45] Date of Patent: Aug. 4, 1998

[54] DEVELOPMENT OF RESEARCH DIAGNOSTIC AND PRODUCTION TOOLS FOR PRO-HORMONE CONVERTASES

[75] Inventors: Nabil G. Seidah, Ile-des-Soeurs; Michel Chrétien, Montréal, both of Canada

[73] Assignee: Institut de Recherches Cliniques de Montreal, Montreal, Canada

[21] Appl. No.: 712,241

[22] Filed: Sep. 12, 1996

Related U.S. Application Data

[63] Continuation of Ser. No. 529,785, Sep. 18, 1995, abandoned, which is a continuation of Ser. No. 963,535, Oct. 20, 1992, abandoned.

[51] Int. Cl.[6] .................... C07H 21/04

[52] U.S. Cl. .................... 536/23.5; 536/24.3

[58] Field of Search .................... 536/23.5, 23.51, 536/24.3, 24.31, 24.33

[56] References Cited

U.S. PATENT DOCUMENTS 5,288,612 2/1994 Griffin et al. .................... 435/23

OTHER PUBLICATIONS

Barr, P.J., et al. (1991). DNA and Cell Biol. 10(5):319–328.
Basak, A., et al. (1990). Int. J. Peptide Protein Res. 36:7–17.
Basak, A., et al. (1992). Journal of Chromatography 581:17–29.
Benjannet, S., et al. (1991). Proc. Natl. Acad. Sci. USA. 88:3564–3568.
Bradbury, A.F., et al. (1982). Nature 298:686–688.
Bresnahan, P.A., et al. (1990). J. Cell. Biol. 111:2851–2859.
Bryan, P., et al. (1986). Proc. Natl. Acad. Sci. USA 83:3743–3745.
Burgess, T.L., et al. (1987). Annu. Rev. Cell. Biol. 3:243–293.
Cathala, et al. (1983). DNA 2(4):329–335.
Chakrabarti S., et al. (1985). Molecular and Cellular Biology 5(12):3403–3409.
Christie, D.L., et al. (1984). J. Biol. Chem. 266(24):15679–15683.
Cooper, J.A., et al. (1984). J. Biol. Chem. 259(12):7835–7841.
Creemers, J.W.M., et al. (1992). FEBS. 300(1):82–88.
Davison, A.J., et al. (1990). Nucleic Acids Research. 18(14):4285–4286.
Fricker, L.D., et al. (1990). J. Biol. Chem. 265(5):2476–2482.
Fuller, R.S., et al. (1989). Science. 246:482–486.
Glass, D.B., et al. (1986). J. Biol. Chem. 261(6):2987–2993.
Hakes, D.J., et al. (1991). Endocrinology 129(6):3053–3063.
Hales, C.N., et al. (1980). Methods in Enzymology. 70:334–355.
Hatsuzawa, K., et al. (1990). J. Biol. Chem. 265(36):22075–22078.
Hruby, D.E., et al. (1986). Methods in Enzymology. 124:295–309.
Julius, D., et al. (1984). Cell 37:1075–1089.
Kozak, M. (1989). J. Cell Biol. 108:229–241.
Linde, S., et al. (1983). Methods in Enzymology. 92:309–335.
Mackin, R.B., et al. (1991). Endocrinology. 129(4):2263–2265.
Mizuno, K. et al. (1988). Biochem. Biophys. Res. Commun. 156(1):246–254.
Moss, B., et al. (1990). Nature. 348:91–92.
Roebroek, A.J.M., et al. (1986). EMBO J. 5(9):2197–2202.
Ruoslahti, E. (1988). Annu. Rev. Biochem. 57:375–413.
Sambrook, J., et al. (1989). In "Molecular Cloning. A laboratory manual". Second Edition. Cold Spring Harbor Laboratory Press. p. 1.74.
Saraste, M., et al. (1990). Trends Biochem. Sci. 15:430–434.
Seidah, N.G., et al. (1990). DNA and Cell Biology. 9(6):415–424.
Seidah, N.G., et al. (1991a). Mol. Endocrinol. 5(1):111–122.
Seidah, N.G., et al. (1991b). Genomics. 11:103–107.
Seidah, N.G. et al. (1992). Trends in Endocrinol. Metab. 3(4):133–140.
Seidah, N.G., et al. (1992). DNA and Cell Biol. 11(4):283–289.
Smeekens, S.P., et al. (1990). J. Biol. Chem. 265(6):2997–3000.
Smeekens, S.P., et al. (1991). Proc. Natl. Acad. Sci. USA. 88:340–344.
Van Den Ouweland, A.M.W., et al. (1990). Nucleic Acids Res. 18(3):664.
Van de Ven, W.J.M., et al. (1990). Mol. Biol. Rep. 14:265–275.
Van Vunakis, H. (1980). Methods in Enzymology. 70:201–209.
Von Heijne, G. (1986). Nucleic Acids Res. 14(11):4683–4690.
Okish, R.J., et al. (1990). Proc. Natl. Acad. Sci. USA 87;9378–9382.

*Primary Examiner*—Scott W. Houtteman
*Attorney, Agent, or Firm*—Quarles & Brady

[57] ABSTRACT

The present invention relates to pro-hormone convertases and polypeptidic fragments thereof, nucleic acids encoding them, recombinant viruses expressing these convertases, polyclonal antibodies directed against the convertases, diagnostic kits for the detection and measurement of the convertase content in cell or tissue lysates, culture media or biological fluids by RIA. Diagnostic kits were also developped for detection or measurement of nucleic acids, preferably mRNAs, in cell or tissue lysates by hybridization. The invention also concerns oligonucleotides useful as probes or as primers for DNA synthesis. These oligonucleotides were included in the diagnostic kits as well as used for the obtention of specific fragments of the convertases which have served, together with native convertases, as antigens for the obtention of antibodies. The convertases were produced by mammalian cell lines transfected with the recombinant viruses and purified on affinity columns which are also an object of the invention. Processes for producing the native convertases, fragments thereof and antibodies are also described and claimed.

13 Claims, 8 Drawing Sheets

```
TGTCGACTGTCAGGACCGAAGCGCTTCACTGAGCGCTCGCCGCCGCCCAGCCTCTCCTCTCGCGCCTCCTAGCTCTTCGCAGAGCAACCAGGAGCCAGGAGTGGTCTAGAGCCCGAGGGT 120
                                                                                  -27         -20
                                                                                  MetGluArgArgAlaTrpSerLeuGlnCysThr
GGGAAGGGGGAGTCTGTCTGGCTTTTCTCCTATCTTGCTTCTTTTTCCTCTTCCCTTCCCACTCTTGTTCAAGCGAGTGTGTGAGCTATGGAGCGAAGAGCCTGGAGTCTGCAGTGCACT 240
        -10                 -1↓1                  10                          20
AlaPheValLeuPheCysAlaTrpCysAlaLeuAsnSerAlaLysAlaLysArgGlnPheValAsnGluTrpAlaAlaGluIleProGlyGlyProGluAlaAlaSerAlaIleAlaGlu
GCTTTCGTCCTCTTTTGCGCTTGGTGTGCACTGAACAGTGCAAAAGCGAAAAGGCAATTTGTCAATGAATGGGCAGCGGAGATCCCCGGGGGCCCGGAAGCAGCCTCGGCCATCGCCGAG 360
        30                  40                          50                          60
GluLeuGlyTyrAspLeuLeuGlyGlnIleGlySerLeuGluAsnHisTyrLeuPheLysHisLysAsnHisProArgArgSerArgArgSerAlaPheHisIleThrLysArgLeuSer
GAGCTGGGCTATGACCTTTTGGGTCAGATTGGTTCACTTGAAAATCACTACTTATTCAAACATAAAAACCACCCCAGAAGGTCTCGAAGGAGTGCCTTTCATATCACTAAGAGATTATCT 480
        70                  80         ▼                90                          100
AspAspAspArgValIleTrpAlaGluGlnGlnTyrGluLysGluArgSerLysArgSerAlaLeuArgAspSerAlaLeuAsnLeuPheAsnAspProMetTrpAsnGlnGlnTrpTyr
GATGATGATCGTGTGATATGGGCTGAACAACAGTATGAAAAAGAAAGAAGTAAACGTTCAGCTCTAAGGGACTCAGCACTAAATCTCTTCAATGATCCCATGTGGAATCAGCAATGGTAC 600
                                                                                            ■
        110                 120                         130
LeuGlnAspThrArgMetThrAlaAlaLeuProLysLeuAspLeuHisValIleProValTrpGlnLysGlyIleThrGlyLysGlyValValIleThrValLeuAspAspGlyLeuGlu
TTGCAAGATACCAGGATGACGGCAGCCCTGCCCAAGCTGGACCTTCATGTGATACCTGTTTGGCAAAAAGGCATTACGGGCAAAGGAGTTGTTATCACCGTACTGGATGATGGTTTGGAG 720
 ***    150                 160                         170                         180 ■
TrpAsnHisThrAspIleTyrAlaAsnTyrAspProGluAlaSerTyrAspPheAsnAspAsnAspHisAspProPheProArgTyrAspProThrAsnGluAsnLysHisGlyThrArg
TGGAATCACACGGACATTTATGCCAACTATGATCCAGAGGCTAGCTATGATTTTAATGATAATGACCATGATCCATTTCCCCGATATGATCCCACAAACGAGAACAAACACGGGACCAGA 840
        190                 200                         210                         220
CysAlaGlyGluIleAlaMetGlnAlaAsnAsnHisLysCysGlyValGlyValAlaTyrAsnSerLysValGlyGlyIleArgMetLeuAspGlyIleValThrAspAlaIleGluAla
TGTGCAGGAGAAATTGCCATGCAAGCAAATAATCACAAATGCGGGGTTGGAGTTGCATACAATTCCAAAGTTGGAGGCATAAGAATGCTGGATGGCATTGTGACGGATGCTATTGAGGCC 960
        230                 240                         250                         260
SerSerIleGlyPheAsnProGlyHisValAspIleTyrSerAlaSerTrpGlyProAsnAspAspGlyLysThrValGluGlyProGlyArgLeuAlaGlnLysAlaPheGluTyrGly
AGTTCAATTGGATTCAATCCTGGACACGTGGATATTTACAGTGCAAGCTGGGGCCCTAATGATGATGGGAAAACTGTGGAGGGGCCTGGCCGGCTAGCCCAGAAGGCTTTTGAATATGGT 1080
        270                 280   ■                     290                         300
ValLysGlnGlyArgGlnGlyLysGlySerIlePheValTrpAlaSerGlyAsnGlyGlyArgGlnGlyAspAsnCysAspCysAspGlyTyrThrAspSerIleTyrThrIleSerIle
GTCAAACAGGGGAGACAGGGGAAGGGGTCCATCTTCGTCTGGGCTTCGGGAAACGGGGGGCGTCAGGGAGATAATTGTGACTGTGATGGCTACACAGACAGCATCTACACCATCTCCATC 1200
        310                 320                         330                         340
SerSerAlaSerGlnGlnGlyLeuSerProTrpTyrAlaGluLysCysSerSerThrLeuAlaThrSerTyrSerSerGlyAspTyrThrAspGlnArgIleThrSerAlaAspLeuHis
AGCAGTGCCTCCCAGCAAGGCCTATCCCCCTGGTACGCTGAGAAGTGCTCCTCCACACTGGCCACCTCTTACAGCAGCGGAGATTACACCGACCAGAGAATCACGAGCGCTGACCTGCAC 1320
        350        ■        360                         370      ***                380
AsnAspCysThrGluThrHisThrGlyThrSerAlaSerAlaProLeuAlaAlaGlyIlePheAlaLeuAlaLeuGluAlaAsnProAsnLeuThrTrpArgAspMetGlnHisLeuVal
```

FIG. 1A

```
AATGACTGCACGGAGACGCACACAGGCACCTCGGCCTCTGCACCTCTGGCTGCTGGCATCTTCGCTCTGGCCCTGGAAGCAAACCCAAATCTCACCTGGCGAGATATGCAGCACCTGGTT  1440
              390                               400                               410                               420
ValTrpThrSerGluTyrAspProLeuAlaAsnAsnProGlyTrpLysLysAsnGlyAlaGlyLeuMetValAsnSerArgPheGlyPheGlyLeuLeuAsnAlaLysAlaLeuValAsp
GTCTGGACCTCTGAGTATGACCCGCTGGCCAATAACCCTGGATGGAAAAAGAATGGAGCAGGCTTGATGGTGAATAGTCGATTTGGATTTGGCTTGCTAAATGCCAAAGCTCTGGTGGAT  1560
              430                               440                               450                               460
LeuAlaAspProArgThrTrpArgSerValProGluLysLysGluCysValValLysAspAsnAspPheGluProArgAlaLeuLysAlaAsnGlyGluValIleIleGluIleProThr
TTAGCTGACCCCAGGACCTGGAGGAGCGTGCCTGAGAAGAAAGAGTGTGTTGTAAAGGACAATGACTTTGAGCCCAGAGCCCTGAAAGCTAATGGAGAAGTTATCATTGAAATTCCAACA  1680
              470                               480                               490                               500
ArgAlaCysGluGlyGlnGluAsnAlaIleLysSerLeuGluHisValGlnPheGluAlaThrIleGluTyrSerArgArgGlyAspLeuHisValThrLeuThrSerAlaAlaGlyThr
AGAGCTTGTGAAGGACAAGAAAATGCTATCAAGTCCCTGGAGCATGTACAATTTGAAGCAACAATTGAATATTCCCGAAGAGGAGACCTTCATGTCACACTTACTTCTGCTGCTGGAACT  1800
              510                               520                               530                               540
SerThrValLeuLeuAlaGluArgGluArgAspThrSerProAsnGlyPheLysAsnTrpAspPheMetSerValHisThrTrpGlyGluAsnProIleGlyThrTrpThrLeuArgIle
AGCACTGTGCTCTTGGCTGAAAGAGAACGGGATACATCTCCTAATGGCTTTAAGAACTGGGACTTCATGTCTGTTCACACATGGGGAGAGAACCCTATAGGTACTTGGACTTTGAGAATT  1920
              550                               560                               570                               580
ThrAspMetSerGlyArgIleGlnAsnGluGlyArgIleValAsnTrpLysLeuIleLeuHisGlyThrSerSerGlnProGluHisMetLysGlnProArgValTyrThrSerTyrAsn
ACAGACATGTCTGGAAGAATTCAAAATGAAGGAAGAATTGTGAACTGGAAGCTGATTTTGCACGGGACCTCTTCTCAGCCAGAGCATATGAAGCAGCCTCGTGTGTACACGTCCTACAAC  2040
              590                               600                               610                               620
ThrValGlnAsnAspArgArgGlyValGluLysMetValAspProGlyGluGluGlnProThrGlnGluAsnProLysGluAsnThrLeuValSerLysSerProSerSerSerSerVal
ACTGTTCAGAATGACAGAAGAGGGGTGGAGAAGATGGTGGATCCAGGGGAGGAGCAGCCCACACAAGAGAACCCTAAGGAGAACACCCTGGTGTCCAAAAGCCCCAGCAGCAGCAGCGTA  2160
              630                               640                               650                               660
GlyGlyArgArgAspGluLeuGluGluGlyAlaProSerGlnAlaMetLeuArgLeuLeuGlnSerAlaPheSerLysAsnSerProProLysGlnSerProLysLysSerProSerAla
GGGGGCCGGAGGGATGAGTTGGAGGAGGGAGCCCCTTCCCAGGCCATGCTGCGACTCCTGCAAAGTGCTTTCAGTAAAAACTCACCGCCAAAGCAATCACCAAAGAAGTCCCCAAGTGCA  2280
              670                               680                               690                               700
LysLeuAsnIleProTyrGluAsnPheTyrGluAlaLeuGluLysLeuAsnLysProSerGlnLeuLysAspSerGluAspSerLeuTyrAsnAspTyrValAspValPheTyrAsnThr
AAGCTCAACATCCCTTATGAAAACTTCTACGAAGCCCTGGAAAAGCTGAACAAACCTTCCCAGCTTAAAGACTCTGAAGACAGTCTGTATAATGACTATGTTGATGTTTTTTATAACACT  2400
              710                               720             726
LysProTyrLysHisArgAspAspArgLeuLeuGlnAlaLeuValAspIleLeuAsnGluGluAsn

AAACCTTACAAGCACAGAGACGACCGGCTGCTTCAAGCTCTGGTGGACATTCTGAATGAGGAAAATTAAAATAAGTGTGTGGTCCCAAGTTGGAAATATTCATGCTTCTTCCTTACCCTG  2520
CGATTTTGCCTGTGTCTGAAGTGGTTGTTTTGTCATGAATTCTTATGCTTATAATATCCTTTGTGGCACCTTTTCTTTTTCTCCCTAAACTGTACATGTGAAGGGGATGAGCTCAAGCAG  2640
GAAGTTCAACTTCCAGAATTGATCATAGGTATTTCAAAACACATCTTTCCTGTCTGCACAAGTGAAGTGTTTTGTTCTTTCTGGAGTCACAGTTGACAAAAAGCTCTTACACTACATTAG  2760
AACACTGCATTAGAGCCCATTTCAATTCTCAAAAGAAAAGGCAAAACCTGGGATATCAATTAATTTGAAAACATAATCTGCAAAGAATGAGAAGGAGTCAGAAACTGTTTCTGTAGCTTG  2880
TTCCCTGTCTTGTCCATGTGGTTCTTCAAATTTTGATGCCAAGAAAGTATTTGGTAGGCCTAATGAAGGAGTTCACTGTAAGACTCATTCCCTAGATCTTTCTATTCCAAAGTGCCACTC  3000
ATTCCTGTAGTCAAAATCTGGTCATGTTGGTCAAAAGCCTGGATTATTTAGATCTAGAAACAGATCTTGAAATCTGAATGCTCTGGTTTGAGCAATTTTCGAACATTCTTTGCCTGGTGC  3120
ACTGTGTCTGTGGTGCCAGAGGCGTCCGTGGATCCAGAGGTGGTTATGACTCGTGCTGCATGCCTGGTCTTTCCTCTGTTTCTCCTTCTGAAAGTTTTCTATACCTGTCTCCTTTCTCAG  3240
CCACAAAATAAATGTTGGGAGAAATGATATATACCACTTTCCCA(A)N                                                                              3284
```

FIG. 1B

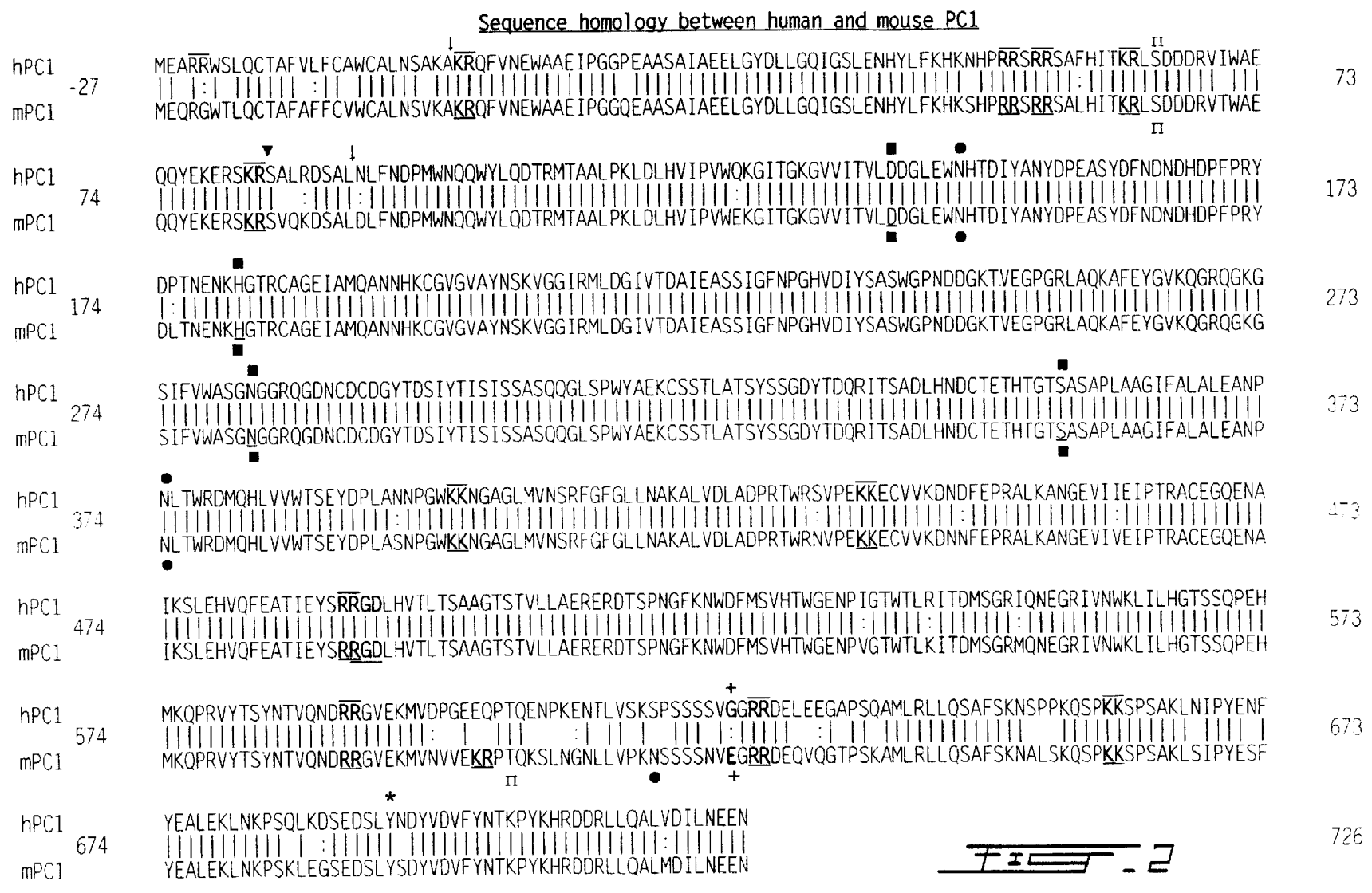

Sequence homology between human and mouse PC1

```
hPC1  -27  MEARRWSLQCTAFVLFCAWCALNSAKAKRQFVNEWAAEIPGGPEAASAIAEELGYDLLGQIGSLENHYLFKHKNHPRRSRRSAFHITKRLSDDDRVIWAE   73
mPC1       MEQRGWTLQCTAFAFFCVWCALNSVKAKRQFVNEWAAEIPGGQEAASAIAEELGYDLLGQIGSLENHYLFKHKSHPRRSRRSALHITKRLSDDDRVTWAE

hPC1   74  QQYEKERSKRSALRDSALNLFNDPMWNQQWYLQDTRMTAALPKLDLHVIPVWQKGITGKGVVITVLDDGLEWNHTDIYANYDPEASYDFNDNDHDPFPRY   173
mPC1       QQYEKERSKRSVQKDSALDLFNDPMWNQQWYLQDTRMTAALPKLDLHVIPVWEKGITGKGVVITVLDDGLEWNHTDIYANYDPEASYDFNDNDHDPFPRY

hPC1  174  DPTNENKHGTRCAGEIAMQANNHKCGVGVAYNSKVGGIRMLDGIVTDAIEASSIGFNPGHVDIYSASWGPNDDGKTVEGPGRLAQKAFEYGVKQGRQGKG   273
mPC1       DLTNENKHGTRCAGEIAMQANNHKCGVGVAYNSKVGGIRMLDGIVTDAIEASSIGFNPGHVDIYSASWGPNDDGKTVEGPGRLAQKAFEYGVKQGRQGKG

hPC1  274  SIFVWASGNGGRQGDNCDCDGYTDSIYTISISSASQQGLSPWYAEKCSSTLATSYSSGDYTDQRITSADLHNDCTETHTGTSASAPLAAGIFALALEANP   373
mPC1       SIFVWASGNGGRQGDNCDCDGYTDSIYTISISSASQQGLSPWYAEKCSSTLATSYSSGDYTDQRITSADLHNDCTETHTGTSASAPLAAGIFALALEANP

hPC1  374  NLTWRDMQHLVVWTSEYDPLANNPGWKKNGAGLMVNSRFGFGLLNAKALVDLADPRTWRSVPEKKECVVKDNDFEPRALKANGEVIIEIPTRACEGQENA   473
mPC1       NLTWRDMQHLVVWTSEYDPLASNPGWKKNGAGLMVNSRFGFGLLNAKALVDLADPRTWRNVPEKKECVVKDNNFEPRALKANGEVIVEIPTRACEGQENA

hPC1  474  IKSLEHVQFEATIEYSRRGDLHVTLTSAAGTSTVLLAERERDTSPNGFKNWDFMSVHTWGENPIGTWTLRITDMSGRIQNEGRIVNWKLILHGTSSQPEH   573
mPC1       IKSLEHVQFEATIEYSRRGDLHVTLTSAAGTSTVLLAERERDTSPNGFKNWDFMSVHTWGENPVGTWTLKITDMSGRMQNEGRIVNWKLILHGTSSQPEH

hPC1  574  MKQPRVYTSYNTVQNDRRGVEKMVDPGEEQPTQENPKENTLVSKSPSSSSVGGRRDELEEGAPSQAMLRLLQSAFSKNSPPKQSPKKSPSAKLNIPYENF   673
mPC1       MKQPRVYTSYNTVQNDRRGVEKMVNVVEKRPTQKSLNGNLLVPKNSSSSNVEGRRDEQVQGTPSKAMLRLLQSAFSKNALSKQSPKKSPSAKLSIPYESF

hPC1  674  YEALEKLNKPSQLKDSEDSLYNDYVDVFYNTKPYKHRDDRLLQALVDILNEEN   726
mPC1       YEALEKLNKPSKLEGSEDSLYSDYVDVFYNTKPYKHRDDRLLQALMDILNEEN
```

FIG. 2

```
                                                                                                           10
ATTTTTTATTTGCATCTTCCCTCTTCGTCCCCTGCTCCACCACCCTGCGCGCCTCACAGCCCCACTTTTCACTCCCAAAGAAGGATGGAGGGCGGTTGTGGATCCCAGTGGAAGGCGGCC 120
                                                                                    MetGluGlyGlyCysGlySerGlnTrpLysAlaAla
                   20                       30                       40                       50
GGGTTCCTCTTCTGTGTGATGGTTTTTGCGTCTGCCGAGAGACCCGTCTTCACGAATCATTTTCTTGTGGAGTTGCATAAAGACGGAGAGGAAGAGGCTCGCCAAGTTGCAGCAGAACAC 240
GlyPheLeuPheCysValMetValPheAlaSerAlaGluArgProValPheThrAsnHisPheLeuValGluLeuHisLysAspGlyGluGluGluAlaArgGlnValAlaAlaGluHis
                   60         †             70                       80                       90
GGCTTTGGAGTCCGAAAGCTCCCCTTTGCAGAAGGCCTGTATCACTTTTATCACAATGGGCTTGCAAAGGCCAAAAGAAGACGCAGCCTACACCATAAGCGGCAGCTAGAGAGAGACCCC 360
GlyPheGlyValArgLysLeuProPheAlaGluGlyLeuTyrHisPheTyrHisAsnGlyLeuAlaLysAlaLysAlaArgArgSerLeuHisHisLysArgGlnLeuGluArgAspPro
                  100                      110                      120                      130
AGGATAAAGATGGCGCTGCAACAAGAAGGATTTGACCGTAAAAAGAGAGGGTACAGGGACATCAATGAGATTGACATCAACATGAATGATCCTCTCTTTACAAAGCAATGGTACCTGTTC 480
ArgIleLysMetAlaLeuGlnGlnGluGlyPheAspArgLysLysArgGlyTyrArgAspIleAsnGluIleAspIleAsnMetAsnAspProLeuPheThrLysGlnTrpTyrLeuPhe
                  140                      150                      160                 ■     170
AACACTGGGCAAGCCGATGGAACTCCTGGGCTAGACTTGAACGTGGCCGAAGCCTGGGAGCTGGGATACACAGGAAAAGGAGTGACCATTGGAATTATGGATGATGGAATTGACTATCTC 600
AsnThrGlyGlnAlaAspGlyThrProGlyLeuAspLeuAsnValAlaGluAlaTrpGluLeuGlyTyrThrGlyLysGlyValThrIleGlyIleMetAspAspGlyIleAspTyrLeu
                  180                      190                      200                    ■  210
CACCCAGACCTGGCCTACAACTACAACGCTGATGCAAGTTATGACTTCAGCAGCAATGACCCCTACCCATACCCTCGATACACAGATGACTGGTTCAACAGCCATGGAACTAGGTGTGCA 720
HisProAspLeuAlaTyrAsnTyrAsnAlaAspAlaSerTyrAspPheSerSerAsnAspProTyrProTyrProArgTyrThrAspAspTrpPheAsnSerHisGlyThrArgCysAla
                  220                      230                      240                      250
GGAGAAGTTTCTGCTGCAGCCAGCAACAATATCTGTGGAGTCGGCGTAGCATACAACTCCAAGGTGGCAGGGATCCGGATGCTGGACCAGCCCTTTATGACAGACATCATCGAAGCCTCC 840
GlyGluValSerAlaAlaAlaSerAsnAsnIleCysGlyValGlyValAlaTyrAsnSerLysValAlaGlyIleArgMetLeuAspGlnProPheMetThrAspIleIleGluAlaSer
                  260                      270                      280
TCCATCAGCCACATGCCTCAACTGATCGACATCTACAGTGCAAGCTGGGGCCCCACAGACAATGGGAAGACGGTTGATGGGCCCCGAGAGCTCACACTCCAGGCCATGGCTGATGGCGTG 960
SerIleSerHisMetProGlnLeuIleAspIleTyrSerAlaSerTrpGlyProThrAspAsnGlyLysThrValAspGlyProArgGluLeuThrLeuGlnAlaMetAlaAspGlyVal
                  300                    ■ 310                      320                      330
AACAAGGGCCGTGGGGGCAAAGGCAGCATCTATGTGTGGGCCTCTGGGGACGGTGGCAGCTACGATGACTGCAACTGTGACGGCTATGCTTCAAGCATGTGGACCATCTCCATCAACTCA 1080
AsnLysGlyArgGlyGlyLysGlySerIleTyrValTrpAlaSerGlyAspGlyGlySerTyrAspAspCysAsnCysAspGlyTyrAlaSerSerMetTrpThrIleSerIleAsnSer
                  340                      350                      360                      370
GCCATCAATGATGGCAGGACTGCCTTGTATGATGAGAGTTGCTCTTCCACCTTAGCATCCACCTTCAGCAATGGGAGGAAGAGGAATCCTGAGGCTGGTGTGGCTACCACAGACTTGTAT 1200
AlaIleAsnAspGlyArgThrAlaLeuTyrAspGluSerCysSerSerThrLeuAlaSerThrPheSerAsnGlyArgLysArgAsnProGluAlaGlyValAlaThrThrAspLeuTyr
   *              380    ■                 390                      400
GGCAACTGTACTCTGAGACACTCTGGGACATCTGCAGCTGCTCCGGAGGCAGCTGGCGTGTTTGCATTAGCTTTGGAGGCTAACCTGGATCTGACCTGGAGAGACATGCAACATCTGACT 1320
GlyAsnCysThrLeuArgHisSerGlyThrSerAlaAlaAlaProGluAlaAlaGlyValPheAlaLeuAlaLeuGluAlaAsnLeuAspLeuThrTrpArgAspMetGlnHisLeuThr
                  420                      430                      440                      450
GTGCTCACCTCCAAGCGGAACCAGCTTCATGATGAGGTTCATCAGTGGCGACGGAATGGGGTTGGCCTGGAATTTAATCACCTCTTTGGCTACGGAGTCCTTGATGCAGGTGCCATGGTG 1440
ValLeuThrSerLysArgAsnGlnLeuHisAspGluValHisGlnTrpArgArgAsnGlyValGlyLeuGluPheAsnHisLeuPheGlyTyrGlyValLeuAspAlaGlyAlaMetVal
```

FIG. 3A

```
460                                     470                                     480                                     490
AAAATGGCTAAAGACTGGAAAACTGTTCCGGAGAGATTCCATTGTGTGGGAGGCTCTGTGCAGAACCCTGAAAAAATACCACCCACCGGCAAGCTGGTACTGACCCTCAAAACAAATGCA 1560
LysMetAlaLysAspTrpLysThrValProGluArgPheHisCysValGlyGlySerValGlnAsnProGluLysIleProProThrGlyLysLeuValLeuThrLeuLysThrAsnAla
500                                     510         *                           520          *                          530
TGTGAGGGGAAGGAAAACTTCGTCCGCTACCTGGAGCACGTCCAAGCTGTCATCACAGTCAACGCGACCAGGAGAGGAGACCTGAACATCAACATGACCTCCCCAATGGGCACCAAGTCC 1680
CysGluGlyLysGluAsnPheValArgTyrLeuGluHisValGlnAlaValIleThrValAsnAlaThrArgArgGlyAspLeuAsnIleAsnMetThrSerProMetGlyThrLysSer
540                                     550                                     560                                     570
ATTTTGCTGAGCCGGCGTCCCAGAGACGACGACTCCAAGGTGGGCTTTGACAAGTGGCCTTTCATGACCACCCACACCTGGGGGGAGGATGCCCGAGGGACCTGGACCCTGGAGCTGGGG 1800
IleLeuLeuSerArgArgProArgAspAspAspSerLysValGlyPheAspLysTrpProPheMetThrThrHisThrTrpGlyGluAspAlaArgGlyThrTrpThrLeuGluLeuGly
580                                     590                                     600                                     610
TTTGTGGGCAGTGCACCACAGAAGGGGTTGCTGAAGGAATGGACCCTGATGCTTCACGGCACACAGAGCGCCCCATACATCGATCAGGTGGTGAGGGATTACCAGTCTAAGCTGGCCATG 1920
PheValGlySerAlaProGlnLysGlyLeuLeuLysGluTrpThrLeuMetLeuHisGlyThrGlnSerAlaProTyrIleAspGlnValValArgAspTyrGlnSerLysLeuAlaMet
620                                     630                                637
TCCAAGAAGCAGGAGCTGGAGGAAGAGCTGGATGAGGCTGTGGAGAGAAGCCTGCAAAGTATCCTGAGAAAGAACTAGGGCCACGCTTCCGCCTTCACCTCCCCTTCCTCCCCGTCTCTG 2040
SerLysLysGlnGluLeuGluGluGluLeuAspGluAlaValGluArgSerLeuGlnSerIleLeuArgLysAsnEND

CCTCTCCTTGCTCCACAGTTCTGGCAGCCACCAGCCACCCAGCAATTCCTGTTACCCCCGACACAAGCAATCCCAGCCTGGTCTCAAGCTTTGCTCGCTGTCAATGATTATTTTCACTAC 2160

AATGGAAGCAACCGTTTTTATTCTGTAGCCCAAATATAGCGTTCCTACCAACATCT(A)n 2217
```

FIG. 3B

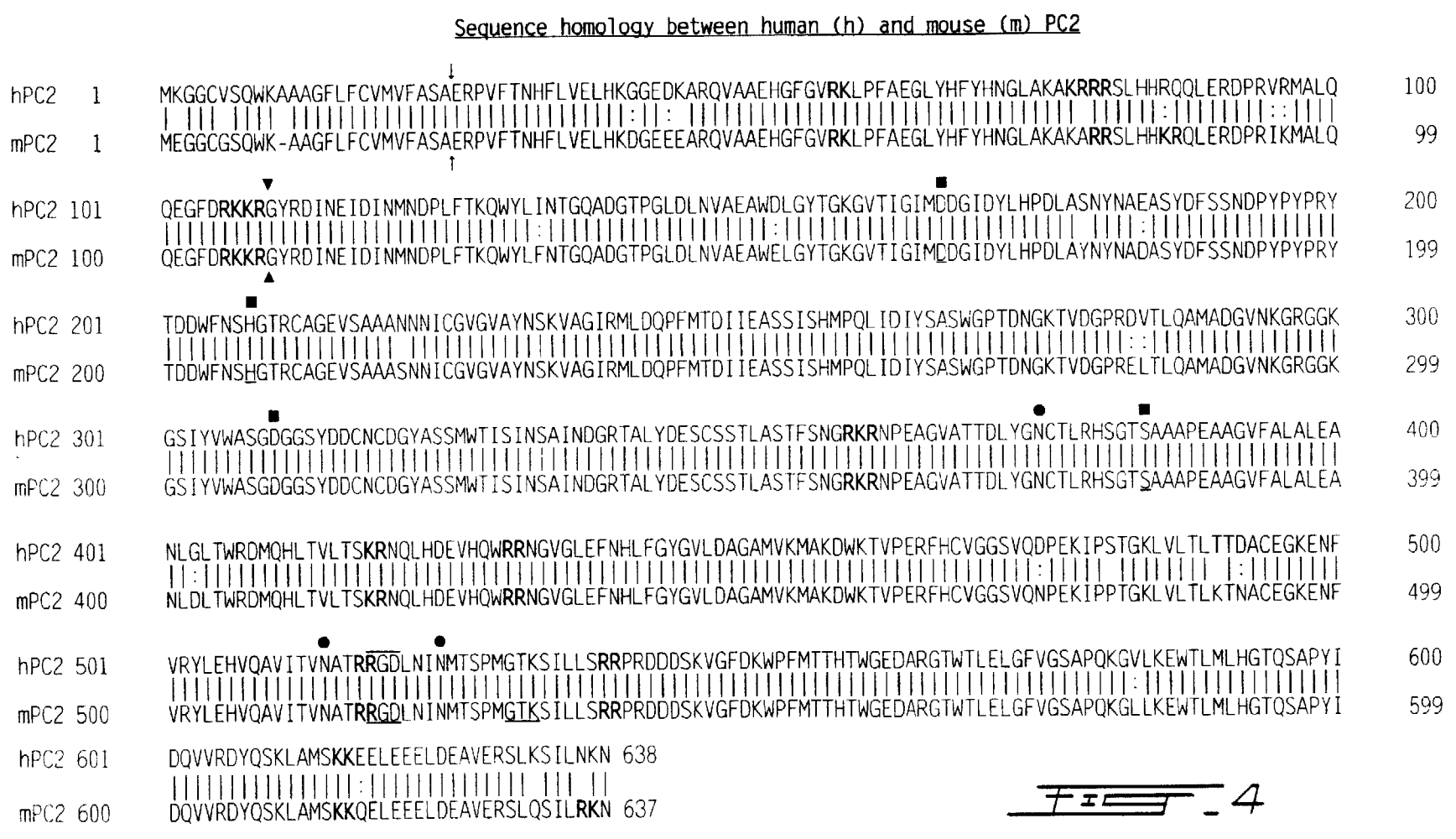

Sequence homology between human (h) and mouse (m) PC2

```
hPC2   1  MKGGCVSQWKAAAGFLFCVMVFASAERPVFTNHFLVELHKGGEDKARQVAAEHGFGVRKLPFAEGLYHFYHNGLAKAKRRRSLHHRQQLERDPRVRMALQ  100
mPC2   1  MEGGCGSQWK-AAGFLFCVMVFASAERPVFTNHFLVELHKDGEEEARQVAAEHGFGVRKLPFAEGLYHFYHNGLAKAKARRSLHHKRQLERDPRIKMALQ   99

hPC2 101  QEGFDRKKRGYRDINEIDINMNDPLFTKQWYLINTGQADGTPGLDLNVAEAWDLGYTGKGVTIGIMDDGIDYLHPDLASNYNAEASYDFSSNDPYPYPRY  200
mPC2 100  QEGFDRKKRGYRDINEIDINMNDPLFTKQWYLFNTGQADGTPGLDLNVAEAWELGYTGKGVTIGIMDDGIDYLHPDLAYNYNADASYDFSSNDPYPYPRY  199

hPC2 201  TDDWFNSHGTRCAGEVSAAANNNICGVGVAYNSKVAGIRMLDQPFMTDIIEASSISHMPQLIDIYSASWGPTDNGKTVDGPRDVTLQAMADGVNKGRGGK  300
mPC2 200  TDDWFNSHGTRCAGEVSAAASNNICGVGVAYNSKVAGIRMLDQPFMTDIIEASSISHMPQLIDIYSASWGPTDNGKTVDGPRELTLQAMADGVNKGRGGK  299

hPC2 301  GSIYVWASGDGGSYDDCNCDGYASSMWTISINSAINDGRTALYDESCSSTLASTFSNGRKRNPEAGVATTDLYGNCTLRHSGTSAAAPEAAGVFALALEA  400
mPC2 300  GSIYVWASGDGGSYDDCNCDGYASSMWTISINSAINDGRTALYDESCSSTLASTFSNGRKRNPEAGVATTDLYGNCTLRHSGTSAAAPEAAGVFALALEA  399

hPC2 401  NLGLTWRDMQHLTVLTSKRNQLHDEVHQWRRNGVGLEFNHLFGYGVLDAGAMVKMAKDWKTVPERFHCVGGSVQDPEKIPSTGKLVLTLTTDACEGKENF  500
mPC2 400  NLDLTWRDMQHLTVLTSKRNQLHDEVHQWRRNGVGLEFNHLFGYGVLDAGAMVKMAKDWKTVPERFHCVGGSVQNPEKIPPTGKLVLTLKTNACEGKENF  499

hPC2 501  VRYLEHVQAVITVNATRRGDLNINMTSPMGTKSILLSRRPRDDDSKVGFDKWPFMTTHTWGEDARGTWTLELGFVGSAPQKGVLKEWTLMLHGTQSAPYI  600
mPC2 500  VRYLEHVQAVITVNATRRGDLNINMTSPMGTKSILLSRRPRDDDSKVGFDKWPFMTTHTWGEDARGTWTLELGFVGSAPQKGLLKEWTLMLHGTQSAPYI  599

hPC2 601  DQVVRDYQSKLAMSKKEELEEELDEAVERSLKSILNKN 638
mPC2 600  DQVVRDYQSKLAMSKKQELEEELDEAVERSLQSILRKN 637
```

FIG. 4

DEVELOPMENT OF RESEARCH DIAGNOSTIC AND PRODUCTION TOOLS FOR PRO-HORMONE CONVERTASES

This is a continuation of application Ser. No. 08/529,785 filed Sep. 18, 1995 now abandoned, which is a continuation of Ser. No. 07/463,535, filed Oct. 20, 1992, now abandoned.

BACKGROUND OF THE INVENTION

Among other proteins, hormones, growth factors, viruses including retroviruses and hormonal receptors often require activation by a specific enzyme or set of enzymes before they can elicit their full biological activity. Such activation is usually made by cleavage of the parent protein, known as pro-protein or precursor, at specific sites usually represented by a pair of basic amino acids of the type LysArg-, ArgArg-, ArgLys- and LysLys-. This initial cleavage is then followed by a number of post-translational modification reactions ultimately leading to the active secretable form of the hormones or proteins. The identification of the yeast Kex2 gene product as the enzyme responsible for the processing of pro-α-mating factor at LysArg- pairs (Julius et al., 1984; Mizuno et al., 1988) provided a molecular prototype of the thought mammalian pro-hormone convertases. The search for the Kex2- like mammalian convertases led to the very recent identification and molecular cloning of three distinct proteinases. These were called Furin (Roebroek et al., 1986; Fuller et al., 1989b; Van Den Ouweland et al., 1990), PC1 (Seidah et al., 1990; 1991a; Smeekens et al., 1991 who also called this enzyme PC3) and PC2 (Smeekens and Steiner, 1990; Seidah et al., 1990). These three enzymes originate from three different genes and their chromosomal localization has been determined in both human and mouse (Seidah et al., 1991b). The organization of the human Furin gene has also been recently reported (Barr et al., 1991) .

Cellular expression of Furin (Bresnahan et al., 1990; Van de Ven et al., 1990; Wise et al., 1990), PC1 and PC2 (Benjannet et al., 1991; Thomas et al., 1991; Hatsuzawa et al., 1990) demonstrated that these proteins are specific proteinases capable of cleaving a number of precursors at pairs of basic residues, of the type LysArg- and ArgArg-, but little cleavage occurred post LysLys-. Furin which is found in most cells, cleaves precursors which emerge from the cell via the constitutive pathway of secretion (Burgess and Kelly, 1987). In contrast, PC1 and PC2 which are only found in endocrine and neuroendocrine cells (Seidah et al., 1990; 1991a), cleave pro-hormones and pro-proteins which negotiate the regulated secretory pathway (Seidah et al., 1992).

So far, the sequence of PC2 obtained from human (hPC2) (Smeekens and Steiner, 1990), mouse (mPC2) (Seidah et al., 1990) and porcine (pPC2) (Seidah et al., in preparation) have been determined. However, only the sequence of mouse PC1 (mPC1) has been reported (Seidah et al., 1990; 1991a; Smeekens et al., 1991). In our search for tissues which express human PC1 (hPC1) transcripts, we noticed that, on Northern blots of human tissues and cell lines, a 6.2 kb mRNA form of hPC1 can be detected when hybridized to the full lenght mouse PC1 (mPC1) cDNA. We have defined the molecular nature of this mRNA and of the protein encoded thereof. Another group discovered at about the same time a nucleic acid and amino acid sequences of hPC1 (Creemers et al., 1992). The coding sequence of the cDNA is the same except for one nucleotide; the nucleotide $A_{1276}$ of the present sequence is replaced by a G in this foreign publication which provoques a change in the amino acid sequence $Ser^{330} \rightarrow Gly$.

The nucleic acid sequence of the cDNAs and the amino acid sequence of the proteins hPC1 and mPC2 so obtained in our laboratory has allowed us to design a series of products useful as research tools and/or in the pharmaceutical field.

As research, therapy and diagnosis of endocrinological disorders, hormone dependant and growth factor dependant pathologies including cancers are very active pharmaceutical fields, there is a need for such tools in developping diagnostic means and curative drugs for such pathologies. Such tools will also be useful in the fabrication of hormones and growth factors in pharmaceutical industry.

STATEMENT OF THE INVENTION

The present invention relates to the nucleic acid sequence of the cDNA encoding the human pro-hormone convertase 1 (hPC1). A human pituitary cDNA library obtained in λgt10 bank has been screened with the full length (2.5 Kb) radiolabeled mouse counterpart of hPC1cDNA: mPC1 cDNA (Seidah et al., 1991a). From the positive clones purified, digested by the restriction enzyme Eco R1 and subcloned in Bluescript II (KS+) plasmid (Stratagene), the nucleic acid sequence of hPC1was obtained by the dideoxy chain termination method performed on double stranded DNA. Any part of said nucleic acid which conserves unique characteristics of hPC1 is also under the scope of the invention.

The invention also concerns recombinant expression vectors containing the full length cDNAs of hPC1 and mPC2, or part thereof, to produce large amounts of these two convertases. Many vectors could be used for achieving such a purpose. For example, adenoviruses, papilloma viruses like SV40 or polyoma viruses, baculoviruses and vaccinia viruses are suitable vectors. Among the latter, the vaccinia virus recombination vectors pVV (Hruby et al., 1986), pMJ-601, -602 (Davison and Moss, 1990) and pTM1 vectors (Moss et al., 1990) usable for transitory expression of the convertase coding sequences are preferred. Any vector being able to express itself in an eucaryotic cell and which use is not intended for producing stably transfected cells by recombination with and insertion in the genome of such cells, but rather used for massive production of the convertases by these cells, and containing the whole cDNA sequence of the convertases or a part thereof are under the scope of this invention provided that said part bear unique characteristics of the convertases. The plasmids offer the avantage of recombination using cloning sites interrupting thymidine kinase gene and easy screening of bacteria containing the recombinants of interest by antibiotics, resistance to which is confered by resistance genes beared by the plasmids. The plasmids of interest are then used for transfection of suitable cell lines.

These recombinant vectors could be extremely useful for the pharmaceutical production of hormones and proteins by modifying the function of a cell as exemplified by the production of αMSH and βEnd from the proopiomelanocortin precursor by the corticotroph cells AtT-20 when transfected with a mPC2 recombinant vaccinia virus (Benjannet et al., 1991). These cells normally do not produce these two hormones because of their very low expression of PC2 gene. They rather produce ACTH and βLPH by the action of PC1 (normally present) on the same precusor.

The invention also relates to the protein hPC1 and part thereof, per se, which can be produced by and purified from the transfected cells expressing it, or synthetized by conventional methods, this synthesis being based on the amino acid sequence of hPC1.

The invention also relates to oligonucleotides specific to various regions of DNA and RNA encoding hPC1 and mPC2. Twelve oligonucleotides have been prepared (six for hPC1 and six for mPC2). The various segments of hPC1 and mPC2 encompassed by these oligonucleotides are: the pro-segment which is lost before the convertases are secreted by the cells, the catalytic segment and the C-terminal segment. These oligonucleotides could be used for detecting nucleic acids encoding these convertases or nucleic acids sharing sufficient homology with these oligonucleotides for allowing hybridization to occur. They could also be used for measuring intracellular levels of convertase mRNAs in lysed cells by hybridization or for detecting or measuring the same in intact cells by in situ hybridization, carried out by standard procedures (Watson et al., 1987). They can also be used as primers of DNA synthesis when paired to any nucleic acid sharing homology.

These oligonucleotides were synthesized and used for PCR amplification of the various segments listed supra in order to clone them in a gene fusion system: pGEX-2T™ plasmid (Pharmacia LKB). After amplification by the host-bacteria, the fusion proteins have been purified from bacterial lysates by affinity chromatography using Glutathione Sepharosem™ 4B (Pharmacia). Cleavage of the GST domain from the fusion protein is facilitated by the Thrombin recognition site present in pGEX-2T™ in proximity of the protein of interest.

The fragments so prepared were used as antigens for immunization of rabbits in order to obtain polyclonal antibodies which are also an object of the invention. Antibodies were directed against the three sets of fragments described supra and against the native proteins obtained by recombinant vaccinia viruses, each for mPC2 and hPC1. A total of eight antibodies was so obtained. These antibodies can achieve multiple purposes: immunoassays (RIA or Elisa), immunohistochemistry or purification of convertases or of any immunologically related proteins, when fixed to a solid matrix.

The availability of specific antibodies directed against various segments of the convertases will allow the user to identify PC1 or PC2 convertases or their various forms in various tissues, cells and fluids. Furthermore, due to the high degree of sequence identity, at least in certain regions, between human and mouse PC1 and PC2, at least one antibody within the series will recognize the enzymes in more than one species. For example, the mPC2/Native antibody will recognize hPC2, and conversely the hPC1/Cat antibody will exhibit a high degree of cross-reactivity with mPC1. These antibodies will thus be useful for both clinical and fundamental reseach. For example, these applications could be:

- the screening of tissues as a method of predicting the possible future development of a tumor, which requires a growth factor and hence of a convertase needed to activate this growth factor, and
- the study of endocrinological pathologies or disorders involving a lack of activity or an overactivity of a convertase.

The invention also relates to affinity columns specially designed for the purification of the convertases PC1 and PC2 or for any protein (including proteinases) having an affinity for the substrate included in these columns. A crude extract of these proteins can be obtained from lysates of cells or of tissues, culture media or biological fluids containing forms of these proteins. The affinity columns allow the obtention of the proteins in a relatively pure form from this crude extract, essential for further work, for example, the obtention of antibodies.

BRIEF STATEMENT OF THE FIGURES

FIG. 1: Complete cDNA (SEQ ID No: 1) and aminoacid (SEQ ID No: 2) sequence of hPC1. The active sites Asp■, Hiss and Serb■, the predicted Asn■ residue as well as the two potential glycosylation sites*** are further emphasized. The predicted site of the signal peptididase cleavage and zymogen activation are depicted by an arrow and an inverted triangle, respectively. The polyadenylation signal AATAAA is found at 35 nts from the poly-A site. The difference between the present coding sequence and the sequence published by Creemers et al. (1992) is shown in boxes.

FIG. 2: Alignment of the primary structures in a single letter notation deduced from the hPC1 (SEQ ID No: 2) (this invention) and mPC1 (SEQ ID No: 3) (Seidah et al., 1991a) cDNA sequences. The active sites Asp■, His■ and Serm■, the predicted Asn■ residue and the basic residues are bold and underlined. The predicted N-glycosylation sites', C-terminal amidation$^{+}$, Ser and Tyr phosphorylation sites$^{\pi}$ are emphasized. The predicted site of cleavage of the signal peptidase is indicated by a vertical arrow.

FIG. 3: Complete cDNA (SEQ ID No: 4) and aminoacid sequence of mPC2. The active sites Asp (■), His (■) and Ser (■), the predicted Asp (■) residue (replacing the expected Asn), as well as the three potential glycosylation sites (*), are indicated. Based on Von Heijne (1986) criteria, the predicted site of the signal peptidase cleavage is depicted by an arrow. The variant polyadenylation signal AATATA is found 18 residues 5' to the poly (A) site. The ArgGlyAsp sequence found at residues 517–519 is also shown.

FIG. 4: Alignment of the primary structure of the hPC2 (SEQ ID No: 6) (Smeekens and Steiner, 1990) and mPC2 (SEQ ID No: 5) (Seidah et al., 1990). The predicted site of cleavage of the signal peptidase is indicated by a vertical arrow. The basic residues are in bold characters. The active sites Asp, His and Ser, and the predicted Asp residue (replacing the expected Asn) are indicated by the ■ symbol. The predicted sites of N-glycosylation are illustrated by a ' symbol. The RGD sequence is underlined.

FIG. 5A–C Northern blot analysis of hPC1transcripts in human tissues, using the hPC1 1938–2558 cRNA probe (SEQ ID No.5). In panels A and B, each lane contains 2 µg of poly-A(+) RNA isolated from the specified human tissues (Clonetech). In pannel C, each lane contains 5 µg of total RNA isolated from 3 individual human pituitaries obtained within 24 hr post-mortem. Some RNA degradation is seen in these pituitary blots. The RNA size markers are indicated in the left blot margin. The exposure times are 7 hr (A,C) and 24 hr(B).

Figures 6A, 6B:
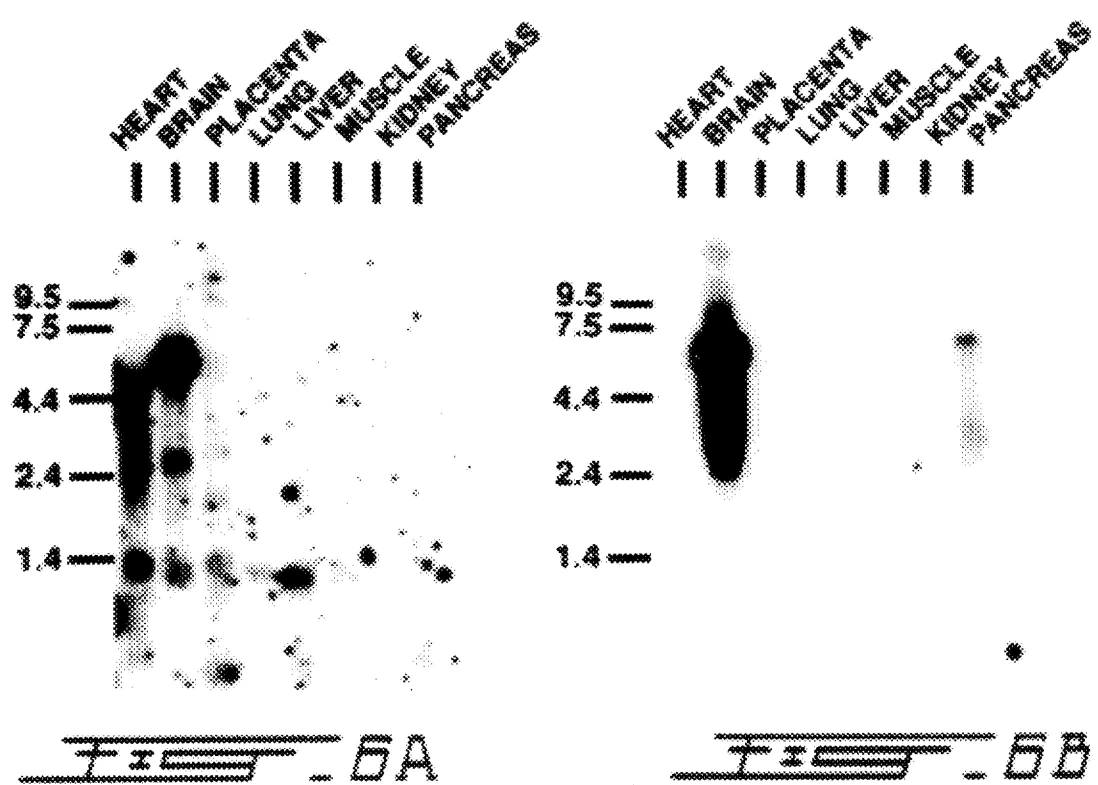

FIG. 6A–B Northern blot analysis of hPC1transcripts in human tissues similar to those in FIG. 5A, using hPC1 1–278 (SEQ ID No: 8) (A) and hPC1 2558–3284 (SEQ ID No: 9) (B) cRNA probes. The exposure times are 41 hr and 24 hr for panels A and B, respectively.

DESCRIPTION OF THE INVENTION

The complete description of the invention will be more readily understood by the following examples which purpose is to illustrate rather than to limit the scope of the invention.

Example 1.

ISOLATION AND SEQUENCE OF THE hPC1 cDNA:

A human pituitary cDNA library established in the λgtlo vector in EcoR1 (kindly provided by Dr. O. Civelli, Vollum Institute, Portland, Oregon) was screened with the full length (2.5 kb) mPC1 cDNA (Seidah et al., 1991a) radiolabeled with [$\alpha$-$^{32}$P] dCTP by the multiple priming method. The plaques were transfered on duplicate filters which were hybridized overnight in a hybridization solution containing about $2\times10^6$ cpm/mL of the radiolabeled mPC1 cDNA (specific activity=114 Ci/mmole) and 4×SET (1×SET=150 mM NaCl, 1 mM $Na_2$EDTA, 30 mM Tris.HCl pH 8.0) at 62° C. Thirteen positive clones were obtained out of a total of $1.5\times10^6$ phage plaques screened. These clones were then repurified by two more screening rounds and phage DNA was isolated from three selected clones which spanned the entire length of the coding region of hPC1. Partial and total EcoR1 digests were subcloned in pBluescript™ II (KS+) (Stratagene) and sequencing was performed on double stranded DNA by the dideoxy chain-termination method, using either the Sequenase™ Kit (US Biochem. Corp.), or the automatic DNA sequencer ALF (Pharmacia), using fluorescent primers and following directives of the manufacturer. A first sequence using the T7 and T3 primers ( which sequences are included in pBluescript II (KS+)) allowed the sequencing of the 5'- and 3'-ends of the inserts. This permitted, in a walking fashion, to synthesize other sense and antisense primers which sequences are determined upon the sequence read in a previous sequencing reaction, allowing the obtention of the complete sequence in both directions.

Composite sequence analysis of these overlapping cDNAs allowed the characterization of the sequence of hPC1starting at the initiator methionine codon and ending at the polyadenylation site. In order to obtain the 5'-end of the hPC1 cDNA sequence, we performed a polymerase chain reaction amplification on the whole cDNA obtained from the λgt10 bank using a λgt10 sense primer ending at the EcoR1 site (of sequence (5' CAGCCTGGTTAAGTCCAAGCTGAATTC 3' (SEQ ID No: 10)) and an hPC1 antisense specific primer I (5' CCTTCGAGACCTTCTGGGGTGG 3', hPC1 nts. 449–428(SEQ ID No: 11)). The amplified cDNA mixture (2%) was then reamplified with the same λgt10 sense primer and a nested hPC1 antisense specific primer II (5' CTGTTCAGTGCACACCAAGCGC 3', hPC1 nts. 278–257(SEQ ID No: 12)). The 300 bp fragment obtained was subcloned in the EcoR1/EcoRV sites of pBluescript II (KS+). The sequence of 5 subclones confirmed that this fragment contained the 5'-end of hPC1 (hPC1 nts. 1–278 (SEQ ID No: 10)).

The PCR reactions were performed in a DNA thermal cycler (Perkin-Elmer, Cetus) Genamp# PCR system 9600 in a volume of 100 μl containing 1 μg cDNA obtained from the human λgt10 pituitary library and, 100 pmol of each primer, 2.5 Units of Taq DNA polymerase (Cetus) in 10 mM Tris (pH 8.3), 50 mM KCl, 1.5 mM $MgCl_2$, and 200 μM dNTPs. The denaturation, annealing and elongation times were for 10, 30 and 40 sec. at temperatures of 94° C., 54° C., and 72° C., respectively.

In FIG. 1, we present the deduced composite cDNA sequence of human PC1, consisting of 3284 nucleotides (SEQ ID No: 1), with a 2259 bp open-reading frame. A consensus polyadenylation signal AATAAA is present as well as the poly A tail appearing 31 nts later. In a similar fashion to mPC1 (Seidah et al., 1991a), we predict, from the structure of hPC1, a 753 amino acid protein (SEQ ID No: 2) with a 27 amino acid signal peptide resulting in a mature 726 amino acid protein. The sequence around the initiator methionine GTGTGAGCT<u>ATG</u>G exhibits a 7/13 nt. identity to the consensus sequence GCCGCC(A/G)CC<u>ATG</u>G for translation initiation in higher eukaryotes (Kozak, 1989), with the purine (G in hPC1) in position -3 being the most highly conserved nucleotide in all eukatyotic mRNAs. Different from the mPC1 structure which predicts three N-glycosylation sites, the amino acid sequence of hPC1 contains only two potential N-glycosylation sites. Assuming a molecular weight contribution of about 2000 daltons for each glycosylation site, we estimate a molecular weight of about 85,000 daltons for the mature hPC1 protein. FIG. 1 also shows that hPC1 contains the three active site amino acids $Asp^{140}$, $His^{181}$ and $Ser^{355}$. These are found at identical positions as in mPC1 and at positions similar to the equivalent residues found in subtilisins, Kex2, furin, and PC2 (Seidah et al., 1990). The $Asn^{282}$ residue important for the stabilization of the oxyanion hole in subtilisins (Bryan et al., 1986) is also present.

The alignment of the predicted protein sequences of human and mouse PC1 is depicted in FIG. 2, from which we calculate a 92.6% overall protein sequence identity of hPC1 and mPC1, with the highest homology (98%) found in the catalytic segment of the molecule comprising residues 84 to 399.

The alignment shown in FIG. 2 also emphasizes the conservation of certain motifs between the human and mouse PC1 sequences, which include:

(1) The presence of 11 pairs of basic residues within the primary sequence of hPC1, as compared to 12 expected from the mPC1 sequence (Seidah et al., 1991a). Notice that no pairs of basic residues are found within the catalytic domain of either hPC1 or mPC1, i.e., from residues 84–399.

(2) In endocrine cells, the potential cleavage of the basic pairs ArgArg- within the sequence (Gly/Glu) $_{625}$GlyArgArg$_{628}$1↓ is expected to generate a C-terminal amidated product at $Gly_{625}$ or $Glu_{625}$ for hPC1 and mPC1 respectively, be the action of the α-amidation enzyme (Bradbury et al., 1982).

(3) An "RGD" structure is found in the sequence ArgArg$_{491}$GlyAsp$_{493}$. This tripeptide sequence which is also found in PC2 (Seidah et al., 1990a; Smeekens and Steiner, 1990) and furin (Roebroek et al., 1986) has been implicated in the adhesion of certain extracellular matrix proteins to cell surface receptors, known as integrins (Ruoslahti, 1988). The function of this surface exposed sequence (Seidah et al., 1991a) in PC1, PC2 and furin is not yet known.

(4) A conserved amphipatic C-terminal structure is found in residues 713–726, possibly implicating a pH-dependent association of PC1 with membranes, in a similar fashion to carboxypeptidase E (Fricker et al., 1990).

(5) At the N-terminus, we find a pro-segment including residues 1–83, which in mammalian cells is excised (by cleavage at the LysArg$_{83}$ pair) in the secreted form of mPC1 and mPC2 (Benjannet et al., in preparation). A similar pro-segment has also been shown to be removed in the granule associated form of bovine PC1 and PC2 (Christie et al., 1991) and in PC2 isolated from anglerfish pancreatic islets (Mackin et al., 1991). Whether such a zymogen activation is performed autocatalytically or by an as yet unidentified proteinase is not yet established.

(6) A putative cAMP/cGMP-dependent protein kinase phosphorylation site (Glass et al., 1986) is seen at $Ser_{64}$ within the pro-segment in both hPC1and mPC1, and at $Thr_{605}$ only in mPC1.

(7) Different from mPC1, hPC1 shows a potential tyrosine protein kinase phosphorylation site (Cooper et al., 1984) at $Tyr_{694}$.

(8) Both hPC1and mPC1 exhibit an ATP/GTP-binding site motif "AA" (also known as the "P-loop") (Saraste et al., 1990), found at residues Gly$_{242}$ProAsnAspAspGlyLysThr$_{249}$. The significance of this motif which is also found at equivalent positions in PC2 and furin is not yet understood.

An other research group has also published the nucleic acid and the amino acid sequences of hPC1 (Creemers et al., 1992). In their case, the coding sequence of the hPC1 cDNA is the same except for one nucleotide; the adenine at position 1276 of the present sequence is replaced by a guanine which results in a change in the amino acid sequence causing the replacement of $Ser^{330}$ by a glycine.

Example 2.

NORTHERN BLOT ANALYSIS:

For Northern analysis, we used a human pituitary total RNA blot and a human multiple tissue Northern blot (Clonetech) of 2 μg of poly $A^+$ RNA from 8 different human tissues (heart, brain, placenta, lung, liver, skeletal muscle, kidney and pancreas). Human pituitary total RNA was extracted from isolated pituitaries by a guanidine isothiocyanate extraction immediately followed by lithium chloride precipitation (Cathala et al., 1983). The pellets were incubated at 42° C. for 3 hr with proteinase K (100 μg/mL) in 0.5% SDS, 50 mM Tris, pH 7.5 and 5 mM EDTA), followed by two phenol chloroform extractions and ethanol precipitation. The samples were run on a horizontal gel apparatus, on a 1.2% agarose gel containing 20 mM HEPES (hP 7.8), 1 mM EDTA and 6% formaldehyde. 10 μg of total RNA was loaded per lane and 2 μg of RNA ladder (9.5, 7.5, 4.4, 2.4, 1.4, 0.24 kilobases) was included in an adjacent lane. The samples were transferred from the gel to a nylon filter (NYTRAN#) by capillary action, and then UV-fixed to the filters.

The three cRNA probes used for Northern analysis were obtained from the segments of hPC1 1–278, 1938–2558, and 2558–3284 inserted in the EcoR1 site of Bluescript# II (KS+) in an antisense fashion to either the T7 or T3 promoters and linearized with SalI, XbaI and BglII, respectively, before reaction with a T7 or T3 RNA polymerase. The filters obtained supra were prehybridized at 62° C. for 2 hr in 400 mM sodium phosphate buffer (pH 7.2) containing 5% SDS, 1 mM EDTA, 1 mg/mL BSA and 50% formamide. Hybridization began with addition of the $^{32}P$-UTP labelled cRNA probe, which was carried out for 16 hr at 62° C.

The filters were washed in 0.1×SSC [1×SSC =0.15M NaCl, 0.015M $Na_3$citrate, pH 7.0], 0.1% SDS, 1 mM EDTA at 75° C. for 2–3 hr, and then exposed to X-ray film with intensifying screens at −70° C. for various times.

The Northern blot analysis of the expression of hPC1 mRNA is depicted in FIGS. 5 and 6, using different cRNA probes. As shown in FIG. 5, using the hPC1 1938–2558 probe (SEQ ID No: 7), one can see that the human brain and pituitary are the major sources of hPC1transcripts and that the size of the major mRNA is estimated to be about 6.2 kb (FIGS. 4A and 4C). Upon over exposure of the blot shown in FIG. 5A, one notice that other tissues also contain some hPC1 transcripts. Notably, as shown in FIG. 5B, on this poly-A (+) RNA blot, the presence of appreciable hPC1mRNA in pancreas is noticeable. Other tissues such as lung, skeletal muscle and heart show the presence of hybridizing bands of which mRNA migrates with apparent sizes either higher (8 kb such as in lung and muscle) or lower 4.8 kb in heart and 1.3 kb in muscle) than the 6.2 kb transcript. The significance of these bands and whether they are related to hPC1or not is not yet known. In an attempt to answer such a question, the poly-A (+) RNA blot was hybridized with two other cRNA probes derived from the hPC1 sequence, namely hPC1 1–278 (SEQ ID No: 8) (FIG. 5A) and hPC1 2558–3284 (SEQ ID No: 9) (FIG. 6B). It can be seen that these probes which represent respectively the 5'- and 3'-ends of the cDNA sequence detect essentially the same 6.2 kb in the brain (FIGS. 6A and 6B), and in the pancreas (FIG. 5B), but do not seem to detect the other bands in muscle and lung. Interestingly, the hPC1 1–278 probe (SEQ ID No: 8) (FIG. 6A) detects more clearly the 4.8 kb band in the heart than either the hPC1 2558–3284 (SEQ ID No: 9) or the hPC1 1938–2558 probes (SEQ ID No: 7) (FIG. 6A).

Since the presented 3.3 kb cDNA (estimated molecular weight) does not account for the major 6.2 kb mRNA of human PC1, one was concerned as to the missing sequence which would clarify the 2.9 kb difference. Also, the size of the 2.8 kb smaller band observed for hPC1in brain (FIG. 6A) is too small to account for the sequenced 3.3 kb. One possibility would be that a cDNA originating from a relatively minor mRNA form found in the pituitary cDNA bank has been isolated. Accordingly, even though the isolated clones all terminated at the same polyadenylation site, alternative polyadenylation sites could be present in hPC1, as was recently reported to be the case for the large mRNA transcripts of rat PC1 and PC2 (Hakes et al., 1991). In agreement, when 5'- extended forms of hPC1 within the cDNA bank by PCR analysis are searched, evidence for the presence of a non-coding 5'-end much longer than the one we presented in FIG. 1 (not shown) was not found. Nevertheless, it is interesting to note that, as compared to mPC1, a cRNA probe prepared from the extended 3'-end sequence found in hPC1(nts. 2558–3284(SEQ ID No: 9)), which hybridized with human PC1 mRNAs (FIG. 5B) failed to detect any mPC1 transcript on Northern blots of mouse neuroendocrine tissues (not shown) known to synthesize large amounts of this enzyme (Seidah et al., 1990; 1991a). This suggests that in hPC1the extended 3'-end sequence is species specific. Creemers et al. (1992) have also found a transcript of 5 Kb which is 2.4 Kb longer than the cloned and sequenced hPC1cDNA. They concluded that a longer 3' stretch could increase the stability of the mRNA.

Example 3.

HOMOLOGY BETWEEN mPC2 AND hPC2:

Alignment of the mouse (SEQ ID No: 5) and human (SEQ ID No: 6) PC2 sequences, as shown in FIGS. 3 and 4, revealed a homology of 88% and 95.9% at the nucleotide and amino acid levels, respectively, with only one gap introduced within the signal peptide sequence of mPC2. This extraordinary conservation of sequence between mouse and human PC2 allow the use of the antibodies made against the enzyme of one species for the detection of the same enzyme in an other species.

Example 4.

GENERATION OF hPC1AND mPC2 VACCINIA VIRUS RECOMBINANTS:

The cDNAs of human PC1 (hPC1) and mouse PC2 (mPC2) were inserted in the sense orientation in expression vectors which produce large amounts of the enzymes when introduced in mammalian cells. These vectors include pVV (Hruby et al., 1986), pMJ-601, 602 (Davison and Moss, 1990) and pTM1 (Moss et al., 1990).

A) Cloning hPC1in plasmid pTM1:

The full length hPC1cDNA (of 3284 base pairs [bp]) was digested from the recombinant plasmid vector Bluescript(+) with the restriction enzymes PstI and Xho1. This cleavage produced the fragments 5' PstI . . . Xho1 3' (length=3044 bp). This isolated fragment was then ligated (using T4 DNA ligase) to the vector pTM1 previously digested with the restriction enzymes NcoI and XhoI with the help of synthetic adaptor consisting of two annealed oligonucleotides, a 27mer (SEQ ID No: 13) and a 19mer (SEQ ID No: 14), the latter having been phosphorylated by T4 polynucleotide kinase. These oligonucleotides have the following sequence: (NcoI) 5' CAT GGA GCG AAG AGC CTG GAG TCT GCA 3' (PstI) (SEQ ID No: 13) 3' CT CGC TTC TCG GAC CTC AGp 5' (SEQ ID No: 14)

Recombinant hPC1 vaccinia viruses can be further obtained with the vectors pMJ601, 602 and $pVV_3$ starting with the plasmid hPC1: TM1. For cloning in pMJ602, the latter was digested with NheI, blunted and digested with SalI while the plasmid hPC1: TM1 was digested with the restriction enzyme NcoI, blunted and then digested with XhoI. Fragments of pMJ602 (7.1 Kb) and of hPC1: TM1 (2.6 Kb) were isolated on 0.5% agarose gel and ligated together. For cloning in pVV, the plasmid hPC1: TM1 was digested with the restriction enzymes NcoI and SstI. In order to receive hPC1 insert, vector $pVV_3$ was previously modified by introducing two annealed oligonucleotides between its restriction sites BamHI and ClaI, these oligonucleotides having the following sequence: 29 mer 5' pGAT CCA CGC GTC CCG GGG GTA CCA TGG AT 3' (SEQ ID No: 15) 27 mer 3' GT GCG CAG GGC CCC CAT GGT ACC TAG C 5' (SEQ ID No: 16)

The resulting plasmid called $pVV_4$ was digested with the enzymes NcoI and SstI. Fragments of 4.1 Kb from $pVV_4$ and 2.4 Kb from hPC1: TM1 were isolated on 0.5% low melting agarose gel and ligated together.

Even if the recombinant plasmid hPC1: MJ601 is not described herein, it is under the scope of the present invention because that would be obvious to any person skilled in the art to obtain such a recombinant plasmid by cleaving pMJ601 and plasmid hPC1: TM1 by appropriate enzymes in such a way that these enzymes produce compatible ends for ligation or rendered compatible by using synthetic linkers.

The above ligated inserts were then propagated in competent *E. Coli* bacteria, prepared and purified from so transformed bacteria by standard techniques (Sambrook et al., 1989).

B) Cloning mPC2 in plasmid pMJ601:

The full length mPC2 cDNA (of 2212 base pairs [bp]) was digested from the recombinant plasmid vector Bluescript(+) with the restriction enzyme BssHII, blunted and digested again with the restriction enzyme HindIII. The fragment of interest was ligated to the plasmid pMJ601 digested with the restriction enzymes SmaI and HindIII. The ligation product was used to transform host bacteria and the propagated plasmid was prepared according to standard techniques (supra). Other recombinant vaccinia viruses (using vaccinia viruses pvv, pMJ602 and pTM1) can be obtained by digesting these plasmids and the starting recombinant material (mPC2: Bluescript) with suitable and compatible restriction enzymes.

C) Transfection of Ltk- cells with pTM1 and pMJ601, 602 recombinant plasmids:

After their production and isolation from the bacteria, the recombinant vectors were used for transfection of the fibroblasts $Ltk^-$ cells in order to obtain recombinant vaccinia viruses expressing hPC1or mPC2.

Before transfection, 6 cm dishes of $Ltk^-$ cells grown in 5 mL MEM (minimal essential medium) containing 10% FBS (fetal bovine serum) and 28 μg/mL gentamycin in 5% $CO_2$ atmosphere, were infected with 0.2 pfu (plaque forming unit) per cell of VV: wt (wild-type vaccinia virus, strain WR) for pMJ601 or 602 recombinants. For pTM1 recombinants, VVmj: β-gal, a vaccinia virus expressing β-galactosidase was used. This virus was obtained upon transfection of the original plasmid pMJ601 in VV:wt infected $Ltk^-$ cells and isolation of a virus producing blue plaques in presence of Bluogal™. For the infection, $Ltk^-$ cells were washed with PBS-M (2.8 MM KCl, 1.5 mM $KH_2PO_4$, 137 mM NaCl, 8 mM $NaHPO_4$ and 1 mM $MgCl_2$) before the addition of the virus diluted in 1 mL PBS-MB (PBS-M +0.01% BSA (bovine serum albumin)). After 30 minutes of incubation at room temperature, the virus inoculum was removed and 3 mL of MEM was added.

For transfection, 50 μl of a DNA composition containing 5 μg of recombinant plasmid, 1 μg vaccinia virus DNA (WT or β-gal, depending of which recombinant is used) and 14 μg salmon sperm DNA in water was mixed with 50 μl Lipofectin™.

This composition was allowed to stand at room temperature for 15 minutes after what, it was transfered into the culture medium. The so transfected cells were incubated at 37° C. overnight after what, 3 mL of MEM supplemented with 20% FBS was added. The cells were incubated again at 37° C. for two more days till crude stocks of recombinant virus were obtained.

D) Preparation of crude stocks of recombinant vaccinia viruses:

The cells were scraped in the medium, centrifuged at 100×g for 5 minutes. The pellet was washed in 5 mL PBS-M, centrifuged at 1000 RPM for 5 minutes and resuspended in 1 mL PBS-M. The cells were frozen and thawed three times, vortexed and sonicated six times ten seconds and kept at -80° C. till use.

E) Isolation of recombinant viruses:

In order to purify the recombinant viruses, 10 $cm^2$ wells of African green monkey kidney cells (BSC-40) were infected with crude stocks of viruses at different dilutions made in PBS-MB. After 30 minutes at room temperature, the non-adsorbed viruses were aspirated and 2 mL MEM supplemented with 10% FBS and 28 μg/mL gentamycin were added. After 2 days of incubation at 37° C., the medium was removed, the cells were washed with 1 mL PBS-M and overlaid with 1.5 mL MEM containing 0.1% Triton X-100™, 450 μg Bluogal™ in 150 μL DMSO (dimethyl sulfoxide) and 1.5% low melting agarose. The cells were incubated at 37° C. till blue plaques appeared showing which cells express β-galactosidase gene. The addition of Triton X-100 dramatically accelerated the apparition of blue plaques. When no Triton was added, no blue plaques appeared before 24 hours, while the addition of Triton expedite the vizualization of positive clones shown by the apparition of blue plaques after 15 minutes of reaction. When blue plaques appeared, plaques of interest were aspirated into the tip of a pipet. In the case of $PVV_4$, pMJ601 or 602 recombinant viruses, blue plaques were picked up while in the case of pTM1 recombinants, white plaques were chosen among blue plaques (Chakrabarti et al., 1985).

Those plaques were mixed with PBS-MB (final volume 0.4 mL), frozen and thawed three times, vortexed and sonicated six times ten seconds and used again to infect BSC-40 cells using the same protocol as exemplified in section E). Cycles of infection were repeated till all plaques in a well of infected cells were blue or white, meaning that the stocks of virus were pure.

F) Preparation of large stocks of vaccinia recombinant viruses:

Large preparations of viruses were obtained by infection of fove 15 cm dishes of BSC-40 cells at a multiplicity of infection of 0.01 pfu per cell. Three days post-infection, the cells were scraped, centrifuged at 100×g for 5 minutes, washed with 10 mL PBS-M, and centrifuged again. The resulting pellet was resuspended in 10 mL of cold Tris-HCl pH 9 (Tris) and homogenized with 25 strokes of a Dounce glass homogenizer. The homogenate was then centrifuged 5 minutes at 200×g. After re-homogenization of the pellet in 10 mL Tris and centrigugation, both supernatants were combined and underlaid with 16 mL of a sucrose pad (36% sucrose in Tris), and spinned at 18,000 RPM for 80 minutes at 4° C. in a SW 27 rotor (Beckman). Supernatant was discarded and the pellet resuspended in 1.5 mL Tris with the help of seven strokes of a Duall Teflon homogenizer. The virus preparation was then aliquoted and kept frozen at −70° C. till used.

Viral DNA was prepared from large preparation of viruses according to the method of Hruby et al. (1986). After verifying that recombinant viruses contained hPC1 or mPC2 by restriction mapping of the viral DNA and by specific raioimmunoassays, the infected cells were used for their massive production. These viruses were also used to infect other cell types than $Ltk^-$ and BSC-40. In order to obtain the native active convertases, cell lines transfectable by these expression vectors must be able to process the convertases because if they are not, the convertases will be produced in an unprocessed form and inactive state. These cell lines might be chosen, for example, between members of the following group of mammalian cell lines: sommatotroph $GH_3$, $GH_4C1$, corticotroph AtT-20, insulinoma βTC3 and pheochromocytoma PC12.

The recombinant vaccinia virus VVtm1: hPC1 consisting of hPC1 inserted in pTM1 recombined with a vaccinia virus containing a β-Galactosidase gene in such a way that the β-Galactosidase gene is removed has been deposited at the American Type Culture Collection under number VR-2589.

The recombinant vaccinia virus VVmj: mPC2 consisting of mPC2 inserted in pMJ601 recombined with a wild-type vaccinia virus has been deposited at the American Type Culture Collection under number VR-2589.

Example 5.

GENERATION OF ACTIVE hPC1 AND mPC2 ANTIGENS:

The BSC-40, the $Ltk^-$ or the suitable mammalian cell lines listed supra (100 mL to 1 liter cultures) were infected with the vaccinia virus recombinants for about 0.5–4 hours and then, the cells were washed and left to incubate overnight according to the protocols detailed in section D). In the case of pTM1 recombinants, a double infection protocol was used. As the gene coding for the convertases is under the control of the T7 RNA polymerase promotor, a second vector encoding the T7 RNA polymerase (vTF7-3; Fuerst et al. (1987)) was used as co-infectant. The secreted material from either the overnight incubation or for a further 1–24 hours in incubation medium with gentamycin and BSA and without serum were collected and provided the starting material to purify the enzymes. Alternatively, the cells were lysed and hPC1or mPC2 extracted from them. The purification of these convertases was achieved according to a procedure developped by the present inventors (as described below). The extracted or secreted products were purified by anion exchange column followed by special affinity columns which were developed using synthetic peptides ending with a reactive group according to the method of Basak et al. (1990). The length and the nature of each immobilized peptide depend upon the specificity of each enzyme, which was determined experimentally using various peptidyl substrates and inhibitors. These substrates and inhibitors were designed on the basis of the sequence of pro-segment of each enzyme. The following sequence was found to be the most potent:

$p^4$ -$p^3$- $p^2$- $p^1$

X -Y - K/R- R-$R^a$ wherein:

i) X represents a basic amino acid residue, preferably one Arg, ii) Y may be Lys, Arg, Ser, Val or Thr, depending of the nature of the enzyme, iii) R and K are the one letter code for Arginine and Lysine, respectively, and iv) $R^a$ represents a reactive group.

The reactive group $R^a$ is a C-terminal modified function which is known to bind to serine proteinases either by non-covalent (reversible) or covalent binding (reversible or non-reversible). The function which has been selected by the present inventors is Semicarbazone (SC: —CH=N—NH—$CONH_2$). Based on earlier work on plasma kallikrein and trypsin (Basak et al., 1990 and 1992), the present inventors have demonstrated that such a function could be adopted to develop affinity ligands, mainly because this function leads to reversible binding, withstands many drastic conditions of pH, ionic strenght, etc. which are sometimes necessary for elution of the bound enzymes, and because columns made of such ligands can be stored for a long period of time at 0° C. in appropriate buffer and pH.

Synthesis of one of the affinity ligands:

First, a fully protected tetrapeptide, Cbz -Arg($NO_2$)-Ser (t-But)- Lys(Boc)- Argininal-SC wherein:

Cbz=Carbobenzyloxy, $NO_2$=nitro, and t-But=ter-butyl, was prepared in solution phase following the scheme 1. It was then hydrogenolysed with $H_2$/Pd black to furnish H-Arg-Ser-Lys(Boc)-Argininal-SC.

SCHEME 1:

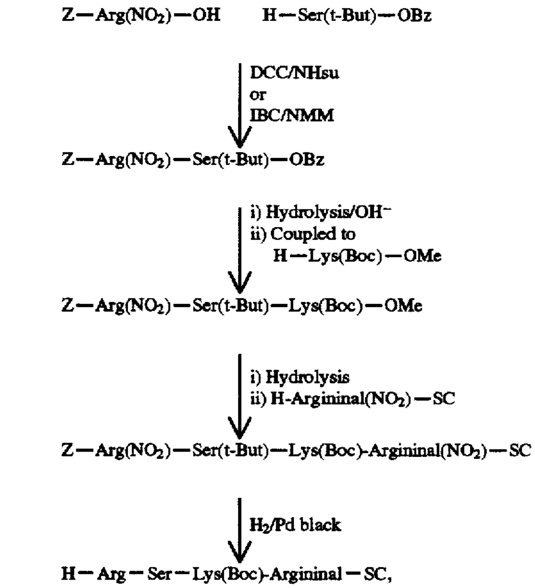

wherein:

OBz: o-benzyl

OMe: o-methyl

DCC: dicyclohexylcarbodiimide,

NHSU: N-hydroxysuccinimide,

IBC: isobutylchloroformate, and

NMM: N-methylmorpholine.

The exemplified peptide ArgSerLysArgininal-SC is the prefered substrate for the purification of the convertase hPC1especially.

These affinity peptides were immobilized via their N-terminal end on a suitable solid matrix, including Affigel-10, -15, Sepharose or other matrices according to a procedure already described by the present inventors (Basak et al., 1990).

H-Arg-Ser-Lys (Boc)-Argininal SC. 2HOAc (4.5 mg, 5.5 μM) was immobilized to Affigel-15 resin (10 mL, packed gel) by shaking at 4° C. in 6 mL of 0.1M $KHCO_3$, pH 8.2. The coupling which was monitored by HPLC, was found to be about 90% after about 18 hours. The resin thus obtained was washed with distilled water (4×10 mL) and again shaken overnight at 4° C. with 15 mL of 1M ethanolamine, pH 9.0 used as a capping reagent in order to destroy the excess of active sites of the resin. The resin was again washed repeatedly with distilled water (about 200 mL) to free from trace amount of ethanolamine. It was then treated with 10 mL of a mixture of Methanol/TFA (1:1, v:v), shaken for 15 minutes at 4° C., filtered, washed with water (4×10 mL), and finally equilibrated with 50 mM NaOAc pH 5.5, before ready to be used.

The affinity columns thus prepared consist of the matrix containing the suitable immobilized peptide derivatives. The purified active enzymes are expected to represent the amino acid residues 84–726 of human PC1 and 85–637 of mPC2, since both PC1 and PC2 loose their pro-domains (1–83 and 1–84 for PC1 and PC2, respectively) before they are secreted from the cells.

After obtaining the convertases produced by cells transfected with recombinant vaccinia viruses, these proteins were purified through a serial combination of an ion exchange and affinity columns, using the following protocol:

100 mL of culture medium containing convertases were concentrated and dialyzed against sodium acetate buffer (NaOAc), pH 5.5 henceforth called acetate buffer using 30 K centriprep filters. The concentrated material (about 10 mL) was passed through an anion exchange column DEAE Sephadex $A_{50}$™ (13×1.5 cm). The column was washed with 30×3 mL of acetate buffer to remove most of the unwanted activity and protein. The enzymes were eluted in 0.6M NaCl/acetate buffer together with some amount of BSA (contained in the medium). In fact, a ratio of about 20: 1 (BSA: convertase; w: w) was obtained in the effluent of this first purification column. As BSA probably helps to stabilize the enzymes, separation of the two proteins at this step was not ameliorated. This combined salt effluent was then dialyzed against acetate buffer and passed through the affinity column Affigel-15-R-S-K-R-SC (supra) (10 mL, 4.5 μM/mL gel). This affinity column allowed up to 99% binding of the convertases. The column was then submitted to consecutive steps of washing with the following buffers: a) acetate buffer, b) 1M NaCl/acetate buffer, c) 10 mM EDTA and 1M NaCl/acetate buffer, d) 100 mM SC.HCl, 1M Guanidine-.HCl and 1M NaCl/acetate buffer and e) 20% Isopropanol/acetate buffer. BSA and other protein impurities were removed in the first three steps while pure convertases were recovered in the last two steps. The percentage of recovery was 50–70%, the loss being mainly caused by degradation. The pure fractions were kept frozen at −20° C. in at least 20% glycerol. At each purification step, the binding and the elution were determined by different methods: a) using the fluorogenic peptide substrate Acetyl-Arg-Ser-Lys-Arg-AMC (AMC: 7-Amino 4-Methyl Coumarin) synthesized by the present inventors, for testing the presence of convertase activity, b) in SDS-acrylamide gel electrophoresis and c) by radioimmunoassay as well as protein assay on each fraction. The fluorogenic substrate recited in a) was used for testing the enzymatic activity recovered, such test being achieved by the following procedure: 20 μL of sample was mixed to 25 μL of 50 mM $CaCl_2$, 25 μL of the fluorogenic substrate dissolved in DMSO and 230 μL of 50 mM NaOAc pH 5.5, and incubated at 37° C. for 6–10 hours. On acrylamide gels, 3 forms of hPC1 were visualized: the major form was the native active form (80–85 Kda) and the two minor forms apparently coming from degradation, had a molecular weight of 66 and 75 Kda, the latter being less abundant.

These purified hPC1and mPC2 enzymes were then used as antigens to inject rabbits and hence generate antibodies against the complete native active convertases.

Example 6.

ANTIGENS GENERATION CONSISTING OF FRAGMENTS OF hPC1AND mPC2 FUSED TO THE C-TERMINUS OF GLUTATHIONE S-TRANSFERASE (GST):

For the production of antibodies against specific domains in hPC1 and mPC2, one method involves the use of synthetic peptide antigens representing sequences at the C-terminus, N-terminus and Pro-segment of each proteinase. Alternatively, a second approach was used. It involves the production of antibodies against fusion proteins to the Glutathione-S-Transferase (GST-) system. This GST is a Gene Fusion System designed to express a gene or gene fragment as a fusion protein. The protein of interest is fused to the carboxyl terminus of glutathione S-transferase from Schistosoma iaPonicum (Smith et al., 1986). The fusion protein is then easily purified from bacterial lysates by affinity chromatography using Glutathione Sepharose 4B (bought from Pharmacia LKB). Cleavage of the Glutathione S-transferase domain from the fusion protein is facilitated by the presence of a Thrombin recognition site. Fusion proteins expressed in the expression vector pGEX-2T (obtained from Pharmacia LKB) may thus be cleaved by Thrombin. The insertion site is as follows:

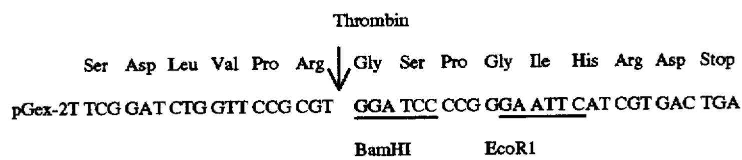

Therefore, the inserted fusion cDNA segment must have at its 5' end a BamH1 site and at its 3' end an EcoR1 site with or without a STOP translation codon. If it does not contain a STOP codon, the fusion protein will have an extra 2 amino acids (ArgAsβ-COOH) at its C-terminus (see above illustration).

This approach was applied to generate antibodies against the pro-sequence, the catalytic and the C-terminal segments of each enzyme. Synthetic oligonucleotides were prepared in order to amplify the specific desired segments of hPC1 and mPC2 by the PCR technique.

hPC1 oligonucleotides 1. hPC1/Pro-segment/BamH1 (Sense Primer) [nucleotides 288–312]
   5' CAGGATCC-AAA AGG CAA TTT GTC AAT GAA TGG G 3'
   (SEQ ID NO:17)
2. hPC1/Junction Pro-Cat/EcoR1 (Antisense Primer) [nts. 561–541]
   5' TTGAATTCTTA-TAG TGC TGA GTC CCT TAG AGC 3'
   (SEQ ID NO:18)
3. hPC1/N-term. Catalytic/BamH1 (Sense Primer) [nts. 538–558]
   5' GTGGATCC-TCA GCT CTA AGG GAC TCA GCA 3'
   (SEQ ID NO:19)
4. hPC1/C-term. Catalytic/EcoR1 (Antisense Primer) [nts. 1755–1735]
   5' TCGAATTCTTA-GGA ATA TTC AAT TGT TGC TTC 3'
   (SEQ ID NO:20)
5. hPC1 (2041–2061)/BamH1 (Sense Primer) [nts. 2173–2193]
   5' GTGGATCC-GAT GAG TTG GAG GAG GGA GCC 3'
   (SEQ ID NO:21) (hPC1 aa629–635)
6. hPC1 (2337–2317)/EcoR1 (Antisense Primer) [nts. 2469–2449]
   5' CAGAATTC-TTA ATT TTC CTC ATT CAG AAT 3'
   (SEQ ID NO:22) (hPC1 aa726–720)

mPC2 oligonucleotides 7. mPC2/Pro-segment/BamH1 (Sense Primer) [nts. 165–184]
   5' CGGGATCC-GAG AGA CCC GTC TTC ACG 3'
   (SEQ ID NO:23)
8. mPC2/Junction Pro-Cat/EcoR1 (Antisense Primer) [nts. 439–419]
   5' CAGAATTCTTA-CTC ATT GAT GTC CCT GTA CCC 3'
   (SEQ ID NO:24)
9. mPC2/N-term. Catalytic/Sma1 (Sense Primer) [nts. 418–429]
   5' AACCCGGG-A GGG TAC AGG GAC ATC AAT GAG 3'
   (SEQ ID NO:25)
10. mPC2/C-term. Catalytic/EcoR1 (Antisense Primer) [nts. 1639–16129]
    5' CAGAATTCTTA-CTC ATT GAT GTC CCT GTA CCC 3'
    (SEQ ID NO:26)
11. mPC2 (1998–1978)/EcoR1 (Antisense Primer) [nts. 2008–1988]
    5' CGGAATT-CTA GTT CTT TCT CAG GAT ACT 3'
    (SEQ ID NO:27) (mPC2 aa637–631)
12. mPC2 (1669–1689)/BamH1 (Sense Primer) [nts. 1679–1699]
    5' CCGGATCC-GGC ACC AAG TCC ATT TTG CTG 3'
    (SEQ ID NO:28) (mPC2 aa529–535)

Therefore, in order to produce fusion proteins against various segments of hPC1 and mPC2, we obtained the desired fragments by applying the technique of Polymerase Chain Reaction (PCR) which allows the amplification of a desired sequence using a pair of oligonucleotides one in a sense and the other in an antisense orientation with respect to the sequence one want to amplify (Erlich, 1989). Therefore, the following pairs of oligonucleotides were used in the PCR reaction:

| Antibody | Pair of oligonucleotides | cDNA sequence** | Amino acids* |
|---|---|---|---|
| hPC1/Pro | #1 and #2 (SEQ ID NO: 17 and 18) | hPC1 (288–561) | hPC1 [1–92] |
| hPC1/Cat | #3 and #4 (SEQ ID NO: 19 and 20) | hPC1 (538–1755) | hPC1 [84–489] |
| hPC1/C-term | #5 and #6 (SEQ ID NO: 21 and 22) | hPC1 (2173–2469) | hPC1 [629–726] |
| mPC2/Pro | #7 and #8 (SEQ ID NO: 23 and 24) | mPC2 (165–439) | mPC2 [1–91] |
| mPC2/Cat | #9 and #10 (SEQ ID NO: 25 and 26) | mPC2 (418–1639) | mPC2 [84–491] |
| mPC2/C-term | #11 and #12 (SEQ ID NO. 27 and 28) | mPC2 (2008–1679) | mPC2 [529–637] |

The numbers refer either to the amino acid* (after the removal of the signal peptide) or to the nucleotide sequence positions**, as reported from the cDNA sequences of hPC1 and mPC2.

The PCR reaction was performed in a DNA thermal cycle (Perkin-Elmer/ Cetus) Genamp™ PCR system 9600 in a volume of 100 µl containing $10^{-8}$ g cDNA obtained from either the hPC1 or mPC2 in Bluescript (+) vector and, 100 pmol of each primer, 2.5 Units of Taq DNA polymerase (Cetus) in 10 mM Tris (pH 8.3), 50 mM KCl, 1.5 mM $MgCl_2$, and 200 µM dNTPs. For 30 repetitive cycles, the denaturation, annealing and elongation times were 10, 30 and 40 sec., at temperatures of 94° C., 54° C., and 72° C., respectively.

The PCR products were purified on a 2% agarose gel, and the electroeluted products were doubly digested with the restriction enzymes BamH1 and EcoR1 and the digestion products were ligated to the pGEX-2™ plasmid which was prior digested with the same restriction enzymes. Transformation of *E. Coli*, the isolation and the preparation of recombinant plasmids were done by standard techniques (Sambrook et al., 1989). The orientation and authenticity of the recombinant plasmids were confirmed by DNA sequencing at the GST-fusion protein junctions.

The bacterial lysates were purified by affinity chromatography column of Glutathione Sepharose 4B™ following the manufacturer's directives (Pharmacia LKB). The purified GST-fusion proteins were then digested with the enzyme Thrombin (Sigma Chemical Co.), following the manufacturer's recommendations. The released fused segments of either PC1 or PC2 (which sizes are shown in the above table) were subjected to N-terminal amino acid microsequence analysis by gas phase sequencing on an Applied Biosystem sequenator to confirm their nature (Seidah and Chretien, 1983).

Once the authenticity of each fragment was verified, the proteins obtained by fusion proteins as well as the native proteins obtained in cells transfected by recombinant vaccinia viruses were injected into rabbits for the development of polyclonal antibodies in order to obtain antibodies. A total of 8 antibodies will allow the definition of the enzymes in any fluid, cell or tissue. For example, if the catalytic- and C-terminal antibodies detect the presence of hPC1 in a tissue, such as a tumor, but the Pro-segment antibody does not, this will mean that the produced hPC1 lacks the pro-segment, most probably meaning that hPC1 is in an active state, as these enzymes are zymogens requiring the removal of their N-terminal pro-segment for maximal activity. In contrast, if the three antibodies detect the same product, then hPC1 will be presumed to be in an inactive state. This information may be useful in the diagnosis of certain endocrine pathologies. For example, human lung cancer is associated with a high production of PC1 (Creemers et al., 1992).

Example 7.

POLYCLONAL ANTIBODIES PRODUCTION:

Recently TiterMax™ #R-1 was introduced in the market by CytRx corporation (150 Technology Parkway, Technological Park/Atlanta. Norcross, Georgia 30092, USA). TiterMax™ #R-1 is a new adjuvant producing a microparticulate emulsion which has the reliability and effectiveness of Freund's Complete Adjuvant (FCA) without the toxic side effects. Groups of female New Zealand White rabbits (N=4) were immunized with the native proteins or fragments thereof (antigens) as follows:

50–100 μg of antigen were injected intramuscularly (IM) in each hind flank (25 μg antigen/50 μl emulsion x 2 injections) on day 1.

50–100 μg of antigen were injected intramuscularly (IM) in each hind flank (25 μg antigen/50 μl emulsion×2 injections) on day 28.

On day 28, 42 and 56 after the first injection, 2–5 mL of blood were withdrawn from each rabbit, centrifuged at 4000×g for minutes and the serum isolated were tested for its antibody titer using $^{125}$I- radioiodinated antigen labeled by either the chloramine T or the Bolton-Hunter methods (Langone, J. J., 1980).

For titer analysis, the serum was initially diluted 100, 200, 500, 1000, 2000, 4000, 5000, and 10,000 folds and the binding of the radioiodinated ligand tested. The serum which gave the highest amount of binding at the highest dilution was considered to have the best antibody titer. The bound radioiodinated ligand was then displaced with non-radioactive antigen at various concentrations from $1\times10^{-12}$ to $1\times10^{-6}$ grams/mL. The shape of the displacement curve obtained defines the specificity and the avidity of the antibody. The animal giving the best titer, specificity and avidity was then chosen for the production of large quantities of antiserum. This rabbit which produced the best titer was then periodically boosted and then bled 14 days later (20–40 mL of blood) and the antibodies stock thus obtained was aliquoted and frozen for future use at −20° C.

Example 8.

DEVELOPMENT OF SPECIFIC RADIOIMMUNOASSAYS (RIAS):

For the development of a specific radioimmunoassay, we used similar procedures published for many other proteins (Van Vunakis, 1980). The specificity of each antiserum was first tested to verify the binding of hPC1 antiserum to mPC2 or mPC1, for example. The ability of each segment-antiserum to recognize the native protein was also tested. This was done by testing whether the binding of the catalytic segment (hPC1/Cat) to the hPC1/Cat antibody could be displaced by the native hPC1protein obtained from vaccinia virus expression vectors, or by another hPC1 segment, hPC1/Pro, for instance.

It was very important to optimize the sensitivity of detection of each antibody in order to increase the chances of its ability to recognize the native protein in various tissue extracts and in plasma. The only antibody for which this optimization will be negative is the one directed against the pro-segment of each convertase, because the pro-segment is absent from the native protein. The first priority lies in the purification of the $^{125}$I-labeled antigen. The latter was purified by reverse-phase HPLC, as reported previously (Seidah and Chretien, 1983; Linde et al., 1983). The sensitivity of the assay was increased by evaluating the best conditions of optimal antigen-antibody binding (Hales and Woodhead, 1980).

Example 9.

DEVELOPMENT OF DIAGNOSTIC KITS:

Radioimmunoassays (RIA):

All 8 kits come complete with the following reagents sufficient for 125 assay tubes ready for use after rehydration:

a) Standard protein b) Rabbit antiserum specific for the protein.

c) $^{125}$I-labeled protein as tracer, 1.5 μCi.

d) Goat anti-rabbit IgG serum.

e) Normal rabbit serum.

f) RIA buffer.

g) Triton X-100/water.

h) Instructions/flow sheet for the RIA protocol.

i) Instructions for calculating the results and graph paper for plotting the results.

Therefore, the hPC1 antibodies kits consist of:

| Kit No. | Antibody Name |
|---|---|
| 1 | hPC1-Native |
| 2 | hPC1/Pro |
| 3 | hPC1/Cat |
| 4 | hPC1/C-term |

and, the mPC2 antibodies kits will consist of:

| | |
|---|---|
| 5 | mPC2-Native |
| 6 | mPC2/Pro |
| 7 | mPC2/Cat |
| 8 | mPC2/C-term |

Hybridization:

The kits should contain all reagents for the preparation of the nucleic acids, preferably mRNAs: buffers for the lysis of cells or tissues, salts and solvents for precipitation of the nucleic acids, extraction buffer like phenol, resuspension buffer, dyes and denaturing agents for electrophoresis, buffers for transfer, buffers for hybridization, labelled oligonucleotides, standardized concentrations of hybridization-positive nucleic acids and, optionally detection means. The oligonucleotides can be the oligonucleotides described in Example 6 labelled by any means known to the person skilled in the art, radioactive nucleotides or by adding fluorescent molecules or molecules reacting with a substrate giving a signal measurable by photometry.

| Symbols for the amino acids | | |
|---|---|---|
| A | Ala | alanine |
| C | Cys | cysteine |
| D | Asp | aspartic acid |
| E | Glu | glumatic acid |
| F | Phe | phenylalanine |
| G | Gly | glycine |
| H | His | histidine |
| I | Ile | isoleucine |
| K | Lys | lysine |
| L | Leu | leucine |
| M | Met | methionine |
| N | Asn | asparagine |
| P | Pro | proline |
| Q | Gln | glutamine |
| R | Arg | arginine |
| S | Ser | serine |
| T | Thr | threonine |
| V | Val | valine |
| W | Trp | tryptophan |
| Y | Tyr | tyrosine |

REFERENCES

BARR et al. (1991). cDNA and gene structure for a human subtilisin-like protease with cleavage specificity for paired basic amino acid residues. DNA and Cell Biol. 10, 319–328.

BASAK, A. et al. (1990). Synthesis of argininal semicarbazone containing peptides and their applications in the affinity chromatography of serine proteinases. Int. J. Peptide. Protein Res. 36, 7–17

BASAK, A. et al. (1992). Affinity purification of proteinases by a combination of immobilized peptidyl aldehyde and semicarbazone. Journal of Chromatography, 581:17–29

BENJANNET et al. (1991). PC1 and PC2 are pro-protein convertases capably of cleaving POMC at distinct pairs of basic residues. Proc. Natl. Acad. Sci. USA 88, 3564–3568.

BRADBURY et al. (1982). Mechanism of C-terminal amide formation by pituitary enzymes. Nature 298, 686–688.

BRESNAHAN et al. (1990). Human for gene encodes a yeast KEX2-like endoprotease that cleaves pro-β-NGF in vivo. J. Cell Biol. 111, 2851–2859.

BRYAN et al. (1986). Site-directed -mutagenesis and the role of the oxyanion hole in subtilisin. Proc. Natl. Acad. Sci. USA 83, 3743–3745.

BURGESS et al. (1987). Constitutive and regulated secretion of proteins. Annu. Rev. Cell Biol. 3, 243–293.

CATHALA et al. (1983). A method for the isolation of intact, translationally active ribonucleic acid. DNA 2, 329–335.

CHAKRABARTI, S. et al. (1985). Vaccinia Virus Expression Vector: Coexpression of β-Galactosidase Provides Visual Screening of Recombinant Virus Plaques. Molecular and Cellular Biology. 5 (12), 3403–3409

CHRISTIE et al. (1991). J. Biol. Chem. 266, 15679–15683.

COOPER et al. (1984). Phosphorylation sites in enolase and lactate dehydrogenase utilized by tyrosine protein kinases in vivo and in vivo. J. Biol. Chem. 259, 7835–7841.

CREEMERS, et al. (1992). Expression in human lung tumor cells of the pro protein processing enzyme PC1/PC3. FEBS. 300 (1), 82–88

DAVISON, et al. (1990). New Vaccinia virus recombiantion plasmids incorporating a synthetic late promotor for high level expression of foreign proteins. Nucleic Acids Research. 18 (14), 4285 4286

ERLICH, S. A. (1989). In "PCR technology: Principles and applications for DNA amplification". Erlich, H. A. ed., Stockton Press, New York FRICKER et al. (1990). Identification of the pH-dependent membrane anchor of carboxypeptidase E (EC 3.4.17.10). J. Biol. Chem. 265, 2476–2482, 1990.

FULLER et al. (1989). Intracellular targeting and structural conservation of a prohormone-processing endoprotease. Science 246, 482–486.

GLASS et al. (1986). Synthetic peptides corresponding to the site phosphorylated in 6-phosphofructo-2-kinase/fructose-2-6-biphosphatase as substrates of cyclic nucleotide-dependent protein kinases. J. Biol. Chem. 261, 2987–2993.

HAKES et al. (1991). Isolation of Two Complementary Deoxyribonucleic Acid Clones from a Rat Insulinoma Cell line Based on Similarities to Kex2 and Furin Sequences and the Specific localization of Each Transcript to Endocrine and Neuroendocrine Tissues in Rats Endocrinology (129)(6)) :3053–3063.

HALES, C. N. et al. (1980). Radioimmunoassays: An overview. Methods in Enzymology. 70, 334–355

HATSUZAWA et al. (1990). Structure and expression of mouse Furin, a yeast Kex2-related protease. J. Biol. Chem. 265, 22075–22078.

HRUBY, D. E. et al. (1986). Use of Vaccinia Virus as a Neuropeptide Expression Vector. Methods in Enzymology. 124, 295–309

JULIUS et al. (1984). Isolation of the putative structural gene for the Lys-Arg- cleaving endopeptidase required for processing of yeast prepro-a-factor. Cell 37, 1075–1089.

KOZAK, M. (1989). The scanning model for translation: an update. J. Cell Biol. 108, 229–241.

LINDE, S. et al. (1983). Preparation of stable radiodinated polypeptide hormones and proteins using polyacrylamide gel electrophoresis. Methods in Enzymology 92, 309–335

MACKIN, R. B. et al. (1991). Identification of a somatostatin-14-generating enzyme as a member of the kex2/furin/PC family. Endocrinology 129, 2263–2265

MIZUNO et al. (1988). Yeast KEX2 gene encodes an endopeptidase homologous to subtilisin-like serine proteases. Biochem. Biophys. Res. Commun. 156, 246–254.

MOSS et al. (1990). New mammalian expression vectors. Nature. 348, 91–92

ROEBROEK et al. (1986). Evolutionary conserved close linkage of the c-fes/fps proto-oncogene and genetic sequences encoding a receptor-like protein. EMBO J. 5, 2197–2202.

RUOSLAHTI, E. (1988). Fibronectin and its receptors. Annu. Rev. Biochem. 57, 375–413.

SAMBROOK, J., Fritsh, E. F. and Maniatis, T. (1989). In "Molecular Cloning. A laboratory manual." Second edition. Cold Spring Harbor Labortory Press.

SARASTE et al. (1990). The P-loop - a common motif in ATP- and GTP-binding proteins. Trends Biochem. Sci. 15, 430–434.

SEIDAH et al. (1990). cDNA sequence of two distinct pituitary proteins homologous to Kex2 and Furin gene products: tissue-specific mRNAs encoding candidates for pro-hormone processing proteinases. DNA and cell Biol. 9, 415–424.

SEIDAH et al. (1991a). Cloning and primary sequence of a mouse candidate pro-hormoneconvertase PC1 homologous to PC2, Furin and Kex2: Distinct chromosomal localization and mRNA distribution in brain and pituitary as compared to PC2. Mol. Endocrinol. 5, 111–122.

SEIDAH et al. (1991b). Chromosomal Assignments of the Genes of the Pro-Protein convertases PC1 (human 5q15–21), PC2 (human 20p11.1–11.2) and Furin (mouse 7[D1-E2 region]). Genomics 11, 103–107.

SEIDAH, N. G. and CHRETIEN, M. (1992). Pro-protein and pro-hormone convertases of the subtilisin family: recent developments and future perspectives. Trends in Endocrinol. Metab. 3 (4): 133–140. SMEEKENS, S. P. and STEINER, D. F. (1990). Identification of a human insulinoma cDNA encoding a novel mammalian protein structurally related to the yeast dibasic processing protease Kex2. J. Biol. Chem. 265, 2997–3000.

SMEEKENS et al. (1991). Identification of a cDNA encoding a second putative prohormone convertase related to PC2 in AtT20 cells and islets of Langerhans. Proc. Natl. Acad. Sci. USA 88, 340–344.

THOMAS et al. (1991). Kex2-like endoproteases PC2 and PC3 accurately cleave model prohormone in mammalian cells: evidence for a common core of neuroendocrine processing enzymes. Proc. Natl. Acad. Sci. USA 88, 5297–5301.

Seidah et al. (1992). The cDNA sequence of the human pro-hormone and pro-protein convertase PC1. DNA and Cell Biol. 11(4):283–289

VAN DEN OUWELAND et al. (1990). Structural homology between the human fur gene product and the subtilisin-like protease encoded by yeast KEX2. Nucleic Acids Res. 81, 664.

VAN DE VEN et al. (1990). Furin is a subtilisin-like proprotein processing enzyme in higher eukaryotes. Mol. Biol. Rep. 14, 265–275.

VON HEIJNE, G. (1986). A new method of predicting signal sequence cleavage sites. Nucleic Acids Res. 14, 4683–4690

VAN VUNAKIS, H. V. (1980). Radioimmunoassays: an overview. Methods in Enzymology, 70, 201–209

WATSON, S. J. et al. (1987). Anatomical localization of mRNA: In situ hybridization of neuropeptide systems. In In Situ Hybridization. Applications to Neurobiolovy.

WISE et al. (1990). Expression of a human proprotein processing enzyme: Correct cleavage of the von Willebrand factor precursor at a paired basic amino acid site. Proc. Natl. Acad. Sci. USA 87, 9378–9382.

What is claimed is:

1. A nucleic acid having the nucleotidic sequence of SEQ ID NO: 1 and wherein nucleotides 208 to 2466 encode human prohormone convertase 1 (hPC1).

2. A recombinant vaccinia virus consisting of a nucleic acid as defined in claim 1 inserted in pTM1 vector and recombined with a vaccinia virus having a β-Galactosidase gene, in such a way that the β-Galactosidase gene is removed and having the ATCC number VR-2589.

3. A kit for detecting and/or measuring the amount of nucleic acids encoding pro-hormone convertase 1, preferably mRNAs, in cultured cells or in tissues of different species comprising at least one pair of oligonucleotides, said pair being selected from the group consisting of SEQ ID NOS: 17/18, 17/20, 17/22, 19/20, 19/22 and 21/22, said pair of oligonucleotides being used as primers to amplify segments of said nucleic acids which are terminated by each member of said pair.

4. A kit for detection of nucleic acids encoding pro-hormone convertase 1, preferably mRNAs, in cultured cells or in tissues of different species comprising at least one oligonucleotide selected from the group consisting of SEQ ID NOS: 17–22, said oligonucleotide being labelled, said label being born by said oligonucleotide or by a first reaction reactive member present on a ligand to said oligonucleotide, said first reactive member reacting with a second reacting member present on said oligonucleotide.

5. A kit for detection of nucleic acids encoding pro-hormone convertase 1, preferably mRNAs, in cultured cells or in tissues of different species comprising at least one probe which is selected from the amplified segments of claim 4.

6. A kit for detecting and/or measuring the amount of nucleic acids encoding pro-hormone convertase 2, preferably mRNAs, in cultured cells or in tissues of different species comprising at least one pair of oligonucleotides, said pair being selected from the group consisting of SEQ ID NOS: 23/24, 23/26, 23/28, 25/26, 25/28 and 27/28, said pair of oligonucleotides being used as primers to amplify segments of said nucleic acids which are terminated by each member of said pair.

7. A kit for detection of nucleic acids encoding pro-hormone convertase 2, preferably mRNAs, in cultured cells or in tissues of different species comprising at least one oligonucleotide selected from the group consisting of SEQ ID NOS: 23 to 28, said oligonucleotide being labelled, said label being born by said oligonucleotide or by a first reactive member present on a ligand to said oligonucleotide, said first reactive member reacting with a second reacting member present on said oligonucleotide.

8. A kit for detection of nucleic acids encoding pro-hormone convertase 2, preferably mRNAs, in cultured cells or in tissues of different species comprising at least one probe which is selected from the amplified segments of claim 6.

9. An isolated and purified nucleic acid encoding human pro-hormone convertase 1 (hPC1).

10. A recombinant expression vector comprising the nucleic acid of claim 9 inserted in an expression vector.

11. A recombinant expression vector according to claim

10, wherein said expression vector is selected from group consisting of pVV, pMJ601, pMJ602 and pTM1.

12. An oligonucleotide having a nucleic acid sequence selected from the group consisting of SEQ ID NOS: 17 to 22.

13. An oligonucleotide having the nucleic acid sequence selected from the group consisting of SEQ ID NOS: 23–28.

* * * * *

SEQUENCE LISTING ( 1 ) GENERAL INFORMATION:

( i i i ) NUMBER OF SEQUENCES: 28

( 2 ) INFORMATION FOR SEQ ID NO: 1:

( i ) SEQUENCE CHARACTERISTICS:
( A ) LENGTH: 3284 base pairs
( B ) TYPE: nucleotide
( C ) STRANDEDNESS: double
( D ) TOPOLOGY: linear ( x i ) SEQUENCE DESCRIPTION: SEQ ID NO: 1:

```
TGTCGACTGT CAGGACCGAA GCGCTTCACT GAGCGCTCGC CGCCGCCCAG     50
CCTCTCCTCT CGCGCCTCCT AGCTCTTCGC AGAGCAACCA GGAGCCAGGA    100
GTGGTCTAGA GCCCGAGGGT GGGAAGGGGG AGTCTGTCTG GCTTTTCTCC    150
TATCTTGCTT CTTTTTCCTC TTCCCTTCCC ACTCTTGTTC AAGCGAGTGT    200
GTGAGCTATG GAGCGAAGAG CCTGGAGTCT GCAGTGCACT GCTTTCGTCC    250
TCTTTTGCGC TTGGTGTGCA CTGAACAGTG CAAAAGCGAA AAGGCAATTT    300
GTCAATGAAT GGGCAGCGGA GATCCCCGGG GGCCCGGAAG CAGCCTCGGC    350
CATCGCCGAG GAGCTGGGCT ATGACCTTTT GGGTCAGATT GGTTCACTTG    400
AAAATCACTA CTTATTCAAA CATAAAAACC ACCCCAGAAG GTCTCGAAGG    450
AGTGCCTTTC ATATCACTAA GAGATTATCT GATGATGATC GTGTGATATG    500
GGCTGAACAA CAGTATGAAA AAGAAAGAAG TAAACGTTCA GCTCTAAGGG    550
ACTCAGCACT AAATCTCTTC AATGATCCCA TGTGGAATCA GCAATGGTAC    600
TTGCAAGATA CCAGGATGAC GGCAGCCCTG CCCAAGCTGG ACCTTCATGT    650
GATACCTGTT TGGCAAAAAG GCATTACGGG CAAAGGAGTT GTTATCACCG    700
TACTGGATGA TGGTTTGGAG TGGAATCACA CGGACATTTA TGCCAACTAT    750
GATCCAGAGG CTAGCTATGA TTTTAATGAT AATGACCATG ATCCATTTCC    800
CCGATATGAT CCCACAAACG AGAACAAACA CGGGACCAGA TGTGCAGGAG    850
AAATTGCCAT GCAAGCAAAT AATCACAAAT GCGGGGTTGG AGTTGCATAC    900
AATTCCAAAG TTGGAGGCAT AAGAATGCTG GATGGCATTG TGACGGATGC    950
TATTGAGGCC AGTTCAATTG GATTCAATCC TGGACACGTG GATATTTACA   1000
GTGCAAGCTG GGGCCCTAAT GATGATGGGA AAACTGTGGA GGGGCCTGGC   1050
CGGCTAGCCC AGAAGGCTTT TGAATATGGT GTCAAACAGG GGAGACAGGG   1100
GAAGGGGTCC ATCTTCGTCT GGGCTTCGGG AAACGGGGGG CGTCAGGGAG   1150
ATAATTGTGA CTGTGATGGC TACACAGACA GCATCTACAC CATCTCCATC   1200
AGCAGTGCCT CCCAGCAAGG CCTATCCCCC TGGTACGCTG AGAAGTGCTC   1250
CTCCACACTG GCCACCTCTT ACAGCAGCGG AGATTACACC GACCAGAGAA   1300
TCACGAGCGC TGACCTGCAC AATGACTGCA CGGAGACGCA CACAGGCACC   1350
TCGGCCTCTG CACCTCTGGC TGCTGGCATC TTCGCTCTGG CCCTGGAAGC   1400
```

-continued

```
AAACCCAAAT CTCACCTGGC GAGATATGCA GCACCTGGTT GTCTGGACCT     1450
CTGAGTATGA CCCGCTGGCC AATAACCCTG GATGGAAAAA GAATGGAGCA     1500
GGCTTGATGG TGAATAGTCG ATTTGGATTT GGCTTGCTAA ATGCCAAAGC     1550
TCTGGTGGAT TTAGCTGACC CCAGGACCTG GAGGAGCGTG CCTGAGAAGA     1600
AAGAGTGTGT TGTAAAGGAC AATGACTTTG AGCCCAGAGC CCTGAAAGCT     1650
AATGGAGAAG TTATCATTGA AATTCCAACA AGAGCTTGTG AAGGACAAGA     1700
AAATGCTATC AAGTCCCTGG AGCATGTACA ATTTGAAGCA ACAATTGAAT     1750
ATTCCCGAAG AGGAGACCTT CATGTCACAC TTACTTCTGC TGCTGGAACT     1800
AGCACTGTGC TCTTGGCTGA AAGAGAACGG GATACATCTC CTAATGGCTT     1850
TAAGAACTGG GACTTCATGT CTGTTCACAC ATGGGGAGAG AACCCTATAG     1900
GTACTTGGAC TTTGAGAATT ACAGACATGT CTGGAAGAAT TCAAAATGAA     1950
GGAAGAATTG TGAACTGGAA GCTGATTTTG CACGGGACCT CTTCTCAGCC     2000
AGAGCATATG AAGCAGCCTC GTGTGTACAC GTCCTACAAC ACTGTTCAGA     2050
ATGACAGAAG AGGGGTGGAG AAGATGGTGG ATCCAGGGGA GGAGCAGCCC     2100
ACACAAGAGA ACCCTAAGGA GAACACCCTG GTGTCCAAAA GCCCCAGCAG     2150
CAGCAGCGTA GGGGGCCGGA GGGATGAGTT GGAGGAGGGA GCCCCTTCCC     2200
AGGCCATGCT GCGACTCCTG CAAAGTGCTT TCAGTAAAAA CTCACCGCCA     2250
AAGCAATCAC CAAAGAAGTC CCCAAGTGCA AAGCTCAACA TCCCTTATGA     2300
AAACTTCTAC GAAGCCCTGG AAAAGCTGAA CAAACCTTCC CAGCTTAAAG     2350
ACTCTGAAGA CAGTCTGTAT AATGACTATG TTGATGTTTT TTATAACACT     2400
AAACCTTACA AGCACAGAGA CGACCGGCTG CTTCAAGCTC TGGTGGACAT     2450
TCTGAATGAG GAAAATTAAA ATAAGTGTGT GGTCCCAAGT TGGAAATATT     2500
CATGCTTCTT CCTTACCCTG CGATTTTGCC TGTGTCTGAA GTGGTTGTTT     2550
TGTCATGAAT TCTTATGCTT ATAATATCCT TTGTGGCACC TTTTCTTTTT     2600
CTCCCTAAAC TGTACATGTG AAGGGGATGA GCTCAAGCAG GAAGTTCAAC     2650
TTCCAGAATT GATCATAGGT ATTTCAAAAC ACATCTTTCC TGTCTGCACA     2700
AGTGAAGTGT TTTGTTCTTT CTGGAGTCAC AGTTGACAAA AAGCTCTTAC     2750
ACTACATTAG AACACTGCAT TAGAGCCCAT TTCAATTCTC AAAAGAAAAG     2800
GCAAAACCTG GGATATCAAT TAATTTGAAA ACATAATCTG CAAAGAATGA     2850
GAAGGAGTCA GAAACTGTTT CTGTAGCTTG TTCCCTGTCT TGTCCATGTG     2900
GTTCTTCAAA TTTTGATGCC AAGAAAGTAT TTGGTAGGCC TAATGAAGGA     2950
GTTCACTGTA AGACTCATTC CCTAGATCTT TCTATTCCAA AGTGCCACTC     3000
ATTCCTGTAG TCAAAATCTG GTCATGTTGG TCAAAAGCCT GGATTATTTA     3050
GATCTAGAAA CAGATCTTGA AATCTGAATG CTCTGGTTTG AGCAATTTTC     3100
GAACATTCTT TGCCTGGTGC ACTGTGTCTG TGGTGCCAGA GGCGTCCGTG     3150
GATCCAGAGG TGGTTATGAC TCGTGCTGCA TGCCTGGTCT TTCCTCTGTT     3200
TCTCCTTCTG AAAGTTTTCT ATACCTGTCT CCTTTCTCAG CCACAAAATA     3250
AATGTTGGGA GAAATGATAT ATACCACTTT CCCA                      3284
```

( 2 ) INFORMATION FOR SEQ ID NO: 2:

( i ) SEQUENCE CHARACTERISTICS:
( A ) LENGTH: 753 amino acids
( B ) TYPE: amino acid
( C ) STRANDEDNESS: single
( D ) TOPOLOGY: linear ( x i ) SEQUENCE DESCRIPTION: SEQ ID NO: 2:

```
Met Glu Arg Arg Ala Trp Ser Leu Gln Cys
                -23                     -18

Thr Ala Phe Val Leu Phe Cys Ala Trp Cys
                -13                      -8

Ala Leu Asn Ser Ala Lys Ala Lys Arg Gln
                 -3                       3

Phe Val Asn Glu Trp Ala Ala Glu Ile Pro
                  8                      13

Gly Gly Pro Glu Ala Ala Ser Ala Ile Ala
                 18                      23

Glu Glu Leu Gly Tyr Asp Leu Leu Gly Gln
                 28                      33

Ile Gly Ser Leu Glu Asn His Tyr Leu Phe
                 38                      43

Lys His Lys Asn His Pro Arg Arg Ser Arg
                 48                      53

Arg Ser Ala Phe His Ile Thr Lys Arg Leu
                 58                      63

Ser Asp Asp Asp Arg Val Ile Trp Ala Glu
                 68                      73

Gln Gln Tyr Glu Lys Glu Arg Ser Lys Arg
                 78                      83

Ser Ala Leu Arg Asp Ser Ala Leu Asn Leu
                 88                      93

Phe Asn Asp Pro Met Trp Asn Gln Gln Trp
                 98                     103

Tyr Leu Gln Asp Thr Arg Met Thr Ala Ala
                108                     113

Leu Pro Lys Leu Asp Leu His Val Ile Pro
                118                     123

Val Trp Gln Lys Gly Ile Thr Gly Lys Gly
                128                     133

Val Val Ile Thr Val Leu Asp Asp Gly Leu
                138                     143

Glu Trp Asn His Thr Asp Ile Tyr Ala Asn
                148                     153

Tyr Asp Pro Glu Ala Ser Tyr Asp Phe Asn
                158                     163

Asp Asn Asp His Asp Pro Phe Pro Arg Tyr
                168                     173

Asp Pro Thr Asn Glu Asn Lys His Gly Thr
                178                     183

Arg Cys Ala Gly Glu Ile Ala Met Gln Ala
                188                     193

Asn Asn His Lys Cys Gly Val Gly Val Ala
                198                     203

Tyr Asn Ser Lys Val Gly Gly Ile Arg Met
                208                     213
```

Leu Asp Gly Ile Val Thr Asp Ala Ile Glu
218 223

Ala Ser Ser Ile Gly Phe Asn Pro Gly His
228 233

Val Asp Ile Tyr Ser Ala Ser Trp Gly Pro
238 243

Asn Asp Asp Gly Lys Thr Val Glu Gly Pro
248 253

Gly Arg Leu Ala Gln Lys Ala Phe Glu Tyr
258 263

Gly Val Lys Gln Gly Arg Gln Gly Lys Gly
268 273

Ser Ile Phe Val Trp Ala Ser Gly Asn Gly
278 283

Gly Arg Gln Gly Asp Asn Cys Asp Cys Asp
288 293

Gly Tyr Thr Asp Ser Ile Tyr Thr Ile Ser
298 303

Ile Ser Ser Ala Ser Gln Gln Gly Leu Ser
308 313

Pro Trp Tyr Ala Glu Lys Cys Ser Ser Thr
318 323

Leu Ala Thr Ser Tyr Ser Ser Gly Asp Tyr
328 333

Thr Asp Gln Arg Ile Thr Ser Ala Asp Leu
338 343

His Asn Asp Cys Thr Glu Thr His Thr Gly
348 353

Thr Ser Ala Ser Ala Pro Leu Ala Ala Gly
358 363

Ile Phe Ala Leu Ala Leu Glu Ala Asn Pro
368 373

Asn Leu Thr Trp Arg Asp Met Gln His Leu
378 383

Val Val Trp Thr Ser Glu Tyr Asp Pro Leu
388 393

Ala Asn Asn Pro Gly Trp Lys Lys Asn Gly
398 403

Ala Gly Leu Met Val Asn Ser Arg Phe Gly
408 413

Phe Gly Leu Leu Asn Ala Lys Ala Leu Val
418 423

Asp Leu Ala Asp Pro Arg Thr Trp Arg Ser
428 433

Val Pro Glu Lys Lys Glu Cys Val Val Lys
438 443

Asp Asn Asp Phe Glu Pro Arg Ala Leu Lys
448 453

Ala Asn Gly Glu Val Ile Ile Glu Ile Pro
458 463

Thr Arg Ala Cys Glu Gly Gln Glu Asn Ala
468 473

Ile Lys Ser Leu Glu His Val Gln Phe Glu
478 483

Ala Thr Ile Glu Tyr Ser Arg Arg Gly Asp
488 493

Leu His Val Thr Leu Thr Ser Ala Ala Gly
498 503

Thr Ser Thr Val Leu Leu Ala Glu Arg Glu
508 513

Arg Asp Thr Ser Pro Asn Gly Phe Lys Asn
518 523

Trp Asp Phe Met Ser Val His Thr Trp Gly
528 533

Glu Asn Pro Ile Gly Thr Trp Thr Leu Arg
538 543

Ile Thr Asp Met Ser Gly Arg Ile Gln Asn
548 553

Glu Gly Arg Ile Val Asn Trp Lys Leu Ile
558 563

Leu His Gly Thr Ser Ser Gln Pro Glu His
568 573

Met Lys Gln Pro Arg Val Tyr Thr Ser Tyr
578 583

Asn Thr Val Gln Asn Asp Arg Arg Gly Val
588 593

Glu Lys Met Val Asp Pro Gly Glu Glu Gln
598 603

Pro Thr Gln Glu Asn Pro Lys Glu Asn Thr
608 613

Leu Val Ser Lys Ser Pro Ser Ser Ser Ser
618 623

Val Gly Gly Arg Arg Asp Glu Leu Glu Glu
628 633

Gly Ala Pro Ser Gln Ala Met Leu Arg Leu
638 643

Leu Gln Ser Ala Phe Ser Lys Asn Ser Pro
648 653

Pro Lys Gln Ser Pro Lys Lys Ser Pro Ser
658 663

Ala Lys Leu Asn Ile Pro Tyr Glu Asn Phe
668 673

Tyr Glu Ala Leu Glu Lys Leu Asn Lys Pro
678 683

Ser Gln Leu Lys Asp Ser Glu Asp Ser Leu
688 693

Tyr Asn Asp Tyr Val Asp Val Phe Tyr Asn
698 703

Thr Lys Pro Tyr Lys His Arg Asp Asp Arg
708 713

Leu Leu Gln Ala Leu Val Asp Ile Leu Asn
718 723

Glu Glu Asn ( 2 ) INFORMATION FOR SEQ ID NO: 3:

( i ) SEQUENCE CHARACTERISTICS:

( A ) LENGTH: 753 amino acids ( B ) TYPE: amino acid
( C ) STRANDEDNESS: single
( D ) TOPOLOGY: linear ( x i ) SEQUENCE DESCRIPTION: SEQ ID NO: 3:

```
Met Glu Gln Arg Gly Trp Thr Leu Gln Cys
                -23                 -18

Thr Ala Phe Ala Phe Phe Cys Val Trp Cys
                -13                  -8

Ala Leu Asn Ser Val Lys Ala Lys Arg Gln
                 -3                   3

Phe Val Asn Glu Trp Ala Ala Glu Ile Pro
                 8                   13

Gly Gly Gln Glu Ala Ala Ser Ala Ile Ala
                18                   23

Glu Glu Leu Gly Tyr Asp Leu Leu Gly Gln
                28                   33

Ile Gly Ser Leu Glu Asn His Tyr Leu Phe
                38                   43

Lys His Lys Ser His Pro Arg Arg Ser Arg
                48                   53

Arg Ser Ala Leu His Ile Thr Lys Arg Leu
                58                   63

Ser Asp Asp Asp Arg Val Thr Trp Ala Glu
                68                   73

Gln Gln Tyr Glu Lys Glu Arg Ser Lys Arg
                78                   83

Ser Val Gln Lys Asp Ser Ala Leu Asp Leu
                88                   93

Phe Asn Asp Pro Met Trp Asn Gln Gln Trp
                98                  103

Tyr Leu Gln Asp Thr Arg Met Thr Ala Ala
                108                 113

Leu Pro Lys Leu Asp Leu His Val Ile Pro
                118                 123

Val Trp Glu Lys Gly Ile Thr Gly Lys Gly
                128                 133

Val Val Ile Thr Val Leu Asp Asp Gly Leu
                138                 143

Glu Trp Asn His Thr Asp Ile Tyr Ala Asn
                148                 153

Tyr Asp Pro Glu Ala Ser Tyr Asp Phe Asn
                158                 163

Asp Asn Asp His Asp Pro Phe Pro Arg Tyr
                168                 173

Asp Leu Thr Asn Glu Asn Lys His Gly Thr
                178                 183

Arg Cys Ala Gly Glu Ile Ala Met Gln Ala
                188                 193

Asn Asn His Lys Cys Gly Val Gly Val Ala
                198                 203

Tyr Asn Ser Lys Val Gly Gly Ile Arg Met
                208                 213

Leu Asp Gly Ile Val Thr Asp Ala Ile Glu
                218                 223
```

Ala Ser Ser Ile Gly Phe Asn Pro Gly His
228 233

Val Asp Ile Tyr Ser Ala Ser Trp Gly Pro
238 243

Asn Asp Asp Gly Lys Thr Val Glu Gly Pro
248 253

Gly Arg Leu Ala Gln Lys Ala Phe Glu Tyr
258 263

Gly Val Lys Gln Gly Arg Gln Gly Lys Gly
268 273

Ser Ile Phe Val Trp Ala Ser Gly Asn Gly
278 283

Gly Arg Gln Gly Asp Asn Cys Asp Cys Asp
288 293

Gly Tyr Thr Asp Ser Ile Tyr Thr Ile Ser
298 303

Ile Ser Ser Ala Ser Gln Gln Gly Leu Ser
308 313

Pro Trp Tyr Ala Glu Lys Cys Ser Ser Thr
318 323

Leu Ala Thr Ser Tyr Ser Ser Gly Asp Tyr
328 333

Thr Asp Gln Arg Ile Thr Ser Ala Asp Leu
338 343

His Asn Asp Cys Thr Glu Thr His Thr Gly
348 353

Thr Ser Ala Ser Ala Pro Leu Ala Ala Gly
358 363

Ile Phe Ala Leu Ala Leu Glu Ala Asn Pro
368 373

Asn Leu Thr Trp Arg Asp Met Gln His Leu
378 383

Val Val Trp Thr Ser Glu Tyr Asp Pro Leu
388 393

Ala Ser Asn Pro Gly Trp Lys Lys Asn Gly
398 403

Ala Gly Leu Met Val Asn Ser Arg Phe Gly
408 413

Phe Gly Leu Leu Asn Ala Lys Ala Leu Val
418 423

Asp Leu Ala Asp Pro Arg Thr Trp Arg Asn
428 433

Val Pro Glu Lys Lys Glu Cys Val Val Lys
438 443

Asp Asn Asn Phe Glu Pro Arg Ala Leu Lys
448 453

Ala Asn Gly Glu Val Ile Val Glu Ile Pro
458 463

Thr Arg Ala Cys Glu Gly Gln Glu Asn Ala
468 473

Ile Lys Ser Leu Glu His Val Gln Phe Glu
478 483

Ala Thr Ile Glu Tyr Ser Arg Arg Gly Asp

```
                488                          493

Leu His Val Thr Leu Thr Ser Ala Ala Gly
                498                          503

Thr Ser Thr Val Leu Leu Ala Glu Arg Glu
                508                          513

Arg Asp Thr Ser Pro Asn Gly Phe Lys Asn
                518                          523

Trp Asp Phe Met Ser Val His Thr Trp Gly
                528                          533

Glu Asn Pro Val Gly Thr Trp Thr Leu Lys
                538                          543

Ile Thr Asp Met Ser Gly Arg Met Gln Asn
                548                          553

Glu Gly Arg Ile Val Asn Trp Lys Leu Ile
                558                          563

Leu His Gly Thr Ser Ser Gln Pro Glu His
                568                          573

Met Lys Gln Pro Arg Val Tyr Thr Ser Tyr
                578                          583

Asn Thr Val Gln Asn Asp Arg Arg Gly Val
                588                          593

Glu Lys Met Val Asn Val Val Glu Lys Arg
                598                          603

Pro Thr Gln Lys Ser Leu Asn Gly Asn Leu
                608                          613

Leu Val Pro Lys Asn Ser Ser Ser Ser Asn
                618                          623

Val Glu Gly Arg Arg Asp Glu Gln Val Gln
                628                          633

Gly Thr Pro Ser Lys Ala Met Leu Arg Leu
                638                          643

Leu Gln Ser Ala Phe Ser Lys Asn Ala Leu
                648                          653

Ser Lys Gln Ser Pro Lys Lys Ser Pro Ser
                658                          663

Ala Lys Leu Ser Ile Pro Tyr Glu Ser Phe
                668                          673

Tyr Glu Ala Leu Glu Lys Leu Asn Lys Pro
                678                          683

Ser Lys Leu Glu Gly Ser Glu Asp Ser Leu
                688                          693

Tyr Ser Asp Tyr Val Asp Val Phe Tyr Asn
                698                          703

Thr Lys Pro Tyr Lys His Arg Asp Asp Arg
                708                          713

Leu Leu Gln Ala Leu Met Asp Ile Leu Asn
                718                          723

Glu Glu Asn
```

( 2 ) INFORMATION FOR SEQ ID NO: 4:

( i ) SEQUENCE CHARACTERISTICS:

( A ) LENGTH: 2217 base pairs ( B ) TYPE: nucleic acid ( C ) STRANDEDNESS: double -continued ( D ) TOPOLOGY: linear ( x i ) SEQUENCE DESCRIPTION: SEQ ID NO: 4:

```
ATTTTTTATT TGCATCTTCC CTCTTCGTCC CCTGCTCCAC CACCCTGCGC     50
GCCTCACAGC CCCACTTTTC ACTCCCAAAG AAGGATGGAG GGCGGTTGTG    100
GATCCCAGTG GAAGGCGGCC GGGTTCCTCT TCTGTGTGAT GGTTTTTGCG    150
TCTGCCGAGA GACCCGTCTT CACGAATCAT TTTCTTGTGG AGTTGCATAA    200
AGACGGAGAG GAAGAGGCTC GCCAAGTTGC AGCAGAACAC GGCTTTGGAG    250
TCCGAAAGCT CCCCTTTGCA GAAGGCCTGT ATCACTTTTA TCACAATGGG    300
CTTGCAAAGG CCAAAAGAAG ACGCAGCCTA CACCATAAGC GGCAGCTAGA    350
GAGAGACCCC AGGATAAAGA TGGCGCTGCA ACAAGAAGGA TTTGACCGTA    400
AAAAGAGAGG GTACAGGGAC ATCAATGAGA TTGACATCAA CATGAATGAT    450
CCTCTCTTTA CAAAGCAATG GTACCTGTTC AACACTGGGC AAGCCGATGG    500
AACTCCTGGG CTAGACTTGA ACGTGGCCGA AGCCTGGGAG CTGGGATACA    550
CAGGAAAAGG AGTGACCATT GGAATTATGG ATGATGGAAT TGACTATCTC    600
CACCCAGACC TGGCCTACAA CTACAACGCT GATGCAAGTT ATGACTTCAG    650
CAGCAATGAC CCCTACCCAT ACCCTCGATA CACAGATGAC TGGTTCAACA    700
GCCATGGAAC TAGGTGTGCA GGAGAAGTTT CTGCTGCAGC CAGCAACAAT    750
ATCTGTGGAG TCGGCGTAGC ATACAACTCC AAGGTGGCAG GGATCCGGAT    800
GCTGGACCAG CCCTTTATGA CAGACATCAT CGAAGCCTCC TCCATCAGCC    850
ACATGCCTCA ACTGATCGAC ATCTACAGTG CAAGCTGGGG CCCCACAGAC    900
AATGGGAAGA CGGTTGATGG GCCCCGAGAG CTCACACTCC AGGCCATGGC    950
TGATGGCGTG AACAAGGGCC GTGGGGGCAA AGGCAGCATC TATGTGTGGG   1000
CCTCTGGGGA CGGTGGCAGC TACGATGACT GCAACTGTGA CGGCTATGCT   1050
TCAAGCATGT GGACCATCTC CATCAACTCA GCCATCAATG ATGGCAGGAC   1100
TGCCTTGTAT GATGAGAGTT GCTCTTCCAC CTTAGCATCC ACCTTCAGCA   1150
ATGGGAGGAA GAGGAATCCT GAGGCTGGTG TGGCTACCAC AGACTTGTAT   1200
GGCAACTGTA CTCTGAGACA CTCTGGGACA TCTGCAGCTG CTCCGGAGGC   1250
AGCTGGCGTG TTTGCATTAG CTTTGGAGGC TAACCTGGAT CTGACCTGGA   1300
GAGACATGCA ACATCTGACT GTGCTCACCT CCAAGCGGAA CCAGCTTCAT   1350
GATGAGGTTC ATCAGTGGCG ACGGAATGGG GTTGGCCTGG AATTTAATCA   1400
CCTCTTTGGC TACGGAGTCC TTGATGCAGG TGCCATGGTG AAAATGGCTA   1450
AAGACTGGAA AACTGTTCCG GAGAGATTCC ATTGTGTGGG AGGCTCTGTG   1500
CAGAACCCTG AAAAAATACC ACCCACCGGC AAGCTGGTAC TGACCCTCAA   1550
AACAAATGCA TGTGAGGGGA AGGAAAACTT CGTCCGCTAC CTGGAGCACG   1600
TCCAAGCTGT CATCACAGTC AACGCGACCA GGAGAGGAGA CCTGAACATC   1650
AACATGACCT CCCCAATGGG CACCAAGTCC ATTTTGCTGA GCCGGCGTCC   1700
CAGAGACGAC GACTCCAAGG TGGGCTTTGA CAAGTGGCCT TTCATGACCA   1750
CCCACACCTG GGGGGAGGAT GCCCGAGGGA CCTGGACCCT GGAGCTGGGG   1800
TTTGTGGGCA GTGCACCACA GAAGGGGTTG CTGAAGGAAT GGACCCTGAT   1850
GCTTCACGGC ACACAGAGCG CCCCATACAT CGATCAGGTG GTGAGGGATT   1900
```

-continued

```
ACCAGTCTAA GCTGGCCATG TCCAAGAAGC AGGAGCTGGA GGAAGAGCTG      1950

GATGAGGCTG TGGAGAGAAG CCTGCAAAGT ATCCTGAGAA AGAACTAGGG      2000

CCACGCTTCC GCCTTCACCT CCCCTTCCTC CCCGTCTCTG CCTCTCCTTG      2050

CTCCACAGTT CTGGCAGCCA CCAGCCACCC AGCAATTCCT GTTACCCCCG      2100

ACACAAGCAA TCCCAGCCTG GTCTCAAGCT TTGCTCGCTG TCAATGATTA      2150

TTTTCACTAC AATGGAAGCA ACCGTTTTTA TTCTGTAGCC CAAATATAGC      2200

GTTCCTACCA ACATCTA                                          2217
```

( 2 ) INFORMATION FOR SEQ ID NO: 5:

( i ) SEQUENCE CHARACTERISTICS:
( A ) LENGTH: 637 amino acids
( B ) TYPE: amino acid
( C ) STRANDEDNESS: single
( D ) TOPOLOGY: linear ( x i ) SEQUENCE DESCRIPTION: SEQ ID NO: 5:

```
Met Glu Gly Gly Cys Gly Ser Gln Trp Lys
                -20                 -15

Ala Ala Gly Phe Leu Phe Cys Val Met Val
                -10                  -5

Phe Ala Ser Ala Glu Arg Pro Val Phe Thr
                  1                   6

Asn His Phe Leu Val Glu Leu His Lys Asp
                 11                  16

Gly Glu Glu Glu Ala Arg Gln Val Ala Ala
                 21                  26

Glu His Gly Phe Gly Val Arg Lys Leu Pro
                 31                  36

Phe Ala Glu Gly Leu Tyr His Phe Tyr His
                 41                  46

Asn Gly Leu Ala Lys Ala Lys Ala Arg Arg
                 51                  56

Ser Leu His His Lys Arg Gln Leu Glu Arg
                 61                  66

Asp Pro Arg Ile Lys Met Ala Leu Gln Gln
                 71                  76

Glu Gly Phe Asp Arg Lys Lys Arg Gly Tyr
                 81                  86

Arg Asp Ile Asn Glu Ile Asp Ile Asn Met
                 91                  96

Asn Asp Pro Leu Phe Thr Lys Gln Trp Tyr
                101                 106

Leu Phe Asn Thr Gly Gln Ala Asp Gly Thr
                111                 116

Pro Gly Leu Asp Leu Asn Val Ala Glu Ala
                121                 126

Trp Glu Leu Gly Tyr Thr Gly Lys Gly Val
                131                 136

Thr Ile Gly Ile Met Asp Asp Gly Ile Asp
                141                 146

Tyr Leu His Pro Asp Leu Ala Tyr Asn Tyr
                151                 156

Asn Ala Asp Ala Ser Tyr Asp Phe Ser Ser
```

-continued

```
                                161                                    166

Asn  Asp  Pro  Tyr  Pro  Tyr  Pro  Arg  Tyr  Thr
                    171                      176

Asp  Asp  Trp  Phe  Asn  Ser  His  Gly  Thr  Arg
                    181                      186

Cys  Ala  Gly  Glu  Val  Ser  Ala  Ala  Ala  Ser
                    191                      196

Asn  Asn  Ile  Cys  Gly  Val  Gly  Val  Ala  Tyr
                    201                      206

Asn  Ser  Lys  Val  Ala  Gly  Ile  Arg  Met  Leu
                    211                      216

Asp  Gln  Pro  Phe  Met  Thr  Asp  Ile  Ile  Glu
                    221                      226

Ala  Ser  Ser  Ile  Ser  His  Met  Pro  Gln  Leu
                    231                      236

Ile  Asp  Ile  Tyr  Ser  Ala  Ser  Trp  Gly  Pro
                    241                      246

Thr  Asp  Asn  Gly  Lys  Thr  Val  Asp  Gly  Pro
                    251                      256

Arg  Glu  Leu  Thr  Leu  Gln  Ala  Met  Ala  Asp
                    261                      266

Gly  Val  Asn  Lys  Gly  Arg  Gly  Gly  Lys  Gly
                    271                      276

Ser  Ile  Tyr  Val  Trp  Ala  Ser  Gly  Asp  Gly
                    281                      286

Gly  Ser  Tyr  Asp  Asp  Cys  Asn  Cys  Asp  Gly
                    291                      296

Tyr  Ala  Ser  Ser  Met  Trp  Thr  Ile  Ser  Ile
                    301                      306

Asn  Ser  Ala  Ile  Asn  Asp  Gly  Arg  Thr  Ala
                    311                      316

Leu  Tyr  Asp  Glu  Ser  Cys  Ser  Ser  Thr  Leu
                    321                      326

Ala  Ser  Thr  Phe  Ser  Asn  Gly  Arg  Lys  Arg
                    331                      336

Asn  Pro  Glu  Ala  Gly  Val  Ala  Thr  Thr  Asp
                    341                      346

Leu  Tyr  Gly  Asn  Cys  Thr  Leu  Arg  His  Ser
                    351                      356

Gly  Thr  Ser  Ala  Ala  Ala  Pro  Glu  Ala  Ala
                    361                      366

Gly  Val  Phe  Ala  Leu  Ala  Leu  Glu  Ala  Asn
                    371                      376

Leu  Asp  Leu  Thr  Trp  Arg  Asp  Met  Gln  His
                    381                      386

Leu  Thr  Val  Leu  Thr  Ser  Lys  Arg  Asn  Gln
                    391                      396

Leu  His  Asp  Glu  Val  His  Gln  Trp  Arg  Arg
                    401                      406

Asn  Gly  Val  Gly  Leu  Glu  Phe  Asn  His  Leu
                    411                      416

Phe  Gly  Tyr  Gly  Val  Leu  Asp  Ala  Gly  Ala
                    421                      426
```

Met Val Lys Met Ala Lys Asp Trp Lys Thr
431 436

Val Pro Glu Arg Phe His Cys Val Gly Gly
441 446

Ser Val Gln Asn Pro Glu Lys Ile Pro Pro
451 456

Thr Gly Lys Leu Val Leu Thr Leu Lys Thr
461 466

Asn Ala Cys Glu Gly Lys Glu Asn Phe Val
471 476

Arg Tyr Leu Glu His Val Gln Ala Val Ile
481 486

Thr Val Asn Ala Thr Arg Arg Gly Asp Leu
491 496

Asn Ile Asn Met Thr Ser Pro Met Gly Thr
501 506

Lys Ser Ile Leu Leu Ser Arg Arg Pro Arg
511 516

Asp Asp Asp Ser Lys Val Gly Phe Asp Lys
521 526

Trp Pro Phe Met Thr Thr His Thr Trp Gly
531 536

Glu Asp Ala Arg Gly Thr Trp Thr Leu Glu
541 546

Leu Gly Phe Val Gly Ser Ala Pro Gln Lys
551 556

Gly Leu Leu Lys Glu Trp Thr Leu Met Leu
561 566

His Gly Thr Gln Ser Ala Pro Tyr Ile Asp
571 576

Gln Val Val Arg Asp Tyr Gln Ser Lys Leu
581 586

Ala Met Ser Lys Lys Gln Glu Leu Glu Glu
591 596

Glu Leu Asp Glu Ala Val Glu Arg Ser Leu
601 606

Gln Ser Ile Leu Arg Lys Asn
611

( 2 ) INFORMATION FOR SEQ ID NO: 6:

( i ) SEQUENCE CHARACTERISTICS:
( A ) LENGTH: 638 amino acids
( B ) TYPE: amino acid
( C ) STRANDEDNESS: single
( D ) TOPOLOGY: linear ( x i ) SEQUENCE DESCRIPTION: SEQ ID NO: 6:

Met Lys Gly Gly Cys Val Ser Gln Trp Lys
-21 -16

Ala Ala Ala Gly Phe Leu Phe Cys Val Met
-11 -6

Val Phe Ala Ser Ala Glu Arg Pro Val Phe
-1 5

Thr Asn His Phe Leu Val Glu Leu His Lys
10 15

-continued

Gly Gly Glu Asp Lys Ala Arg Gln Val Ala
20 25

Ala Glu His Gly Phe Gly Val Arg Lys Leu
30 35

Pro Phe Ala Glu Gly Leu Tyr His Phe Tyr
40 45

His Asn Gly Leu Ala Lys Ala Lys Arg Arg
50 55

Arg Ser Leu His His Arg Gln Gln Leu Glu
60 65

Arg Asp Pro Arg Val Arg Met Ala Leu Gln
70 75

Gln Glu Gly Phe Asp Arg Lys Lys Arg Gly
80 85

Tyr Arg Asp Ile Asn Glu Ile Asp Ile Asn
90 95

Met Asn Asp Pro Leu Phe Thr Lys Gln Trp
100 105

Tyr Leu Ile Asn Thr Gly Gln Ala Asp Gly
110 115

Thr Pro Gly Leu Asp Leu Asn Val Ala Glu
120 125

Ala Trp Asp Leu Gly Tyr Thr Gly Lys Gly
130 135

Val Thr Ile Gly Ile Met Asp Asp Gly Ile
140 145

Asp Tyr Leu His Pro Asp Leu Ala Ser Asn
150 155

Tyr Asn Ala Glu Ala Ser Tyr Asp Phe Ser
160 165

Ser Asn Asp Pro Tyr Pro Tyr Pro Arg Tyr
170 175

Thr Asp Asp Trp Phe Asn Ser His Gly Thr
180 185

Arg Cys Ala Gly Glu Val Ser Ala Ala Ala
190 195

Asn Asn Asn Ile Cys Gly Val Gly Val Ala
200 205

Tyr Asn Ser Lys Val Ala Gly Ile Arg Met
210 215

Leu Asp Gln Pro Phe Met Thr Asp Ile Ile
220 225

Glu Ala Ser Ser Ile Ser His Met Pro Gln
230 235

Leu Ile Asp Ile Tyr Ser Ala Ser Trp Gly
240 245

Pro Thr Asp Asn Gly Lys Thr Val Asp Gly
250 255

Pro Arg Asp Val Thr Leu Gln Ala Met Ala
260 265

Asp Gly Val Asn Lys Gly Arg Gly Gly Lys
270 275

Gly Ser Ile Tyr Val Trp Ala Ser Gly Asp
280 285

Gly Gly Ser Tyr Asp Asp Cys Asn Cys Asp
290 295

Gly Tyr Ala Ser Ser Met Trp Thr Ile Ser
300 305

Ile Asn Ser Ala Ile Asn Asp Gly Arg Thr
310 315

Ala Leu Tyr Asp Glu Ser Cys Ser Ser Thr
320 325

Leu Ala Ser Thr Phe Ser Asn Gly Arg Lys
330 335

Arg Asn Pro Glu Ala Gly Val Ala Thr Thr
340 345

Asp Leu Tyr Gly Asn Cys Thr Leu Arg His
350 355

Ser Gly Thr Ser Ala Ala Ala Pro Glu Ala
360 365

Ala Gly Val Phe Ala Leu Ala Leu Glu Ala
370 375

Asn Leu Gly Leu Thr Trp Arg Asp Met Gln
380 385

His Leu Thr Val Leu Thr Ser Lys Arg Asn
390 395

Gln Leu His Asp Glu Val His Gln Trp Arg
400 405

Arg Asn Gly Val Gly Leu Glu Phe Asn His
410 415

Leu Phe Gly Tyr Gly Val Leu Asp Ala Gly
420 425

Ala Met Val Lys Met Ala Lys Asp Trp Lys
430 435

Thr Val Pro Glu Arg Phe His Cys Val Gly
440 445

Gly Ser Val Gln Asp Pro Glu Lys Ile Pro
450 455

Ser Thr Gly Lys Leu Val Leu Thr Leu Thr
460 465

Thr Asp Ala Cys Glu Gly Lys Glu Asn Phe
470 475

Val Arg Tyr Leu Glu His Val Gln Ala Val
480 485

Ile Thr Val Asn Ala Thr Arg Arg Gly Asp
490 495

Leu Asn Ile Asn Met Thr Ser Pro Met Gly
500 505

Thr Lys Ser Ile Leu Leu Ser Arg Arg Pro
510 515

Arg Asp Asp Asp Ser Lys Val Gly Phe Asp
520 525

Lys Trp Pro Phe Met Thr Thr His Thr Trp
530 535

Gly Glu Asp Ala Arg Gly Thr Trp Thr Leu
540 545

Glu Leu Gly Phe Val Gly Ser Ala Pro Gln

```
                                550                           555

Lys  Gly  Val  Leu  Lys  Glu  Trp  Thr  Leu  Met
                    560                      565

Leu  His  Gly  Thr  Gln  Ser  Ala  Pro  Tyr  Ile
                    570                      575

Asp  Gln  Val  Val  Arg  Asp  Tyr  Gln  Ser  Lys
                    580                      585

Leu  Ala  Met  Ser  Lys  Lys  Glu  Glu  Leu  Glu
                    590                      595

Glu  Glu  Leu  Asp  Glu  Ala  Val  Glu  Arg  Ser
                    600                      605

Leu  Lys  Ser  Ile  Leu  Asn  Lys  Asn
                    610
```

( 2 ) INFORMATION FOR SEQ ID NO: 7:

( i ) SEQUENCE CHARACTERISTICS:
( A ) LENGTH: 621 base pairs
( B ) TYPE: nucleic acid
( C ) STRANDEDNESS: single
( D ) TOPOLOGY: linear ( x i ) SEQUENCE DESCRIPTION: SEQ ID NO: 7:

```
AATTCAAAAT GAAGGAAGAA TTGTGAACTG GAAGCTGATT TTGCACGGGA    50
CCTCTTCTCA GCCAGAGCAT ATGAAGCAGC CTCGTGTGTA CACGTCCTAC   100
AACACTGTTC AGAATGACAG AAGAGGGGTG GAGAAGATGG TGGATCCAGG   150
GGAGGAGCAG CCCACACAAG AGAACCCTAA GGAGAACACC CTGGTGTCCA   200
AAAGCCCCAG CAGCAGCAGC GTAGGGGGCC GGAGGGATGA GTTGGAGGAG   250
GGAGCCCCT  TCCCAGGCCAT GCTGCGACTC CTGCAAAGTG CTTTCAGTAA   300
AAACTCACC  GCCAAAGCAAT CACCAAAGAA GTCCCCAAGT GCAAAGCTCA   350
ACATCCCTT  ATGAAAACTTC TACGAAGCCC TGGAAAAGCT GAACAAACCT   400
TCCCAGCTT  AAAGACTCTGA AGACAGTCTG TATAATGACT ATGTTGATGT   450
TTTTTATAA  CACTAAACCTT ACAAGCACAG AGACGACCGG CTGCTTCAAG   500
CTCTGGTGG  ACATTCTGAAT GAGGAAAATT AAAATAAGTG TGTGGTCCCA   550
AGTTGGAAA  TATTCATGCTT CTTCCTTACC CTGCGATTTT GCCTGTGTCT   600
GAAGTGGTT  GTTTTGTCATG A                                 621
```

( 2 ) INFORMATION FOR SEQ ID NO: 8:

( i ) SEQUENCE CHARACTERISTICS:
( A ) LENGTH: 278 base pairs
( B ) TYPE: nucleotide
( C ) STRANDEDNESS: single
( D ) TOPOLOGY: linear ( x i ) SEQUENCE DESCRIPTION: SEQ ID NO: 8:

```
TGTCGACTGT CAGGACCGAA GCGCTTCACT GAGCGCTCGC CGCCGCCCAG    50
CCTCTCCTCT CGCGCCTCCT AGCTCTTCGC AGAGCAACCA GGAGCCAGGA   100
GTGGTCTAGA GCCCGAGGGT GGGAAGGGGG AGTCTGTCTG GCTTTTCTCC   150
TATCTTGCTT CTTTTTCCTC TTCCCTTCCC ACTCTTGTTC AAGCGAGTGT   200
GTGAGCTATG GAGCGAAGAG CCTGGAGTCT GCAGTGCACT GCTTTCGTCC   250
TCTTTTGCGC TTGGTGTGCA CTGAACAG                           278
```

( 2 ) INFORMATION FOR SEQ ID NO: 9:

( i ) SEQUENCE CHARACTERISTICS:
( A ) LENGTH: 727 base pairs
( B ) TYPE: nucleotide
( C ) STRANDEDNESS: single
( D ) TOPOLOGY: linear ( x i ) SEQUENCE DESCRIPTION: SEQ ID NO: 9:

```
AATTCTTATG CTTATAATAT CCTTTGTGGC ACCTTTTCTT TTTCTCCCTA      50
AACTGTACAT GTGAAGGGGA TGAGCTCAAG CAGGAAGTTC AACTTCCAGA     100
ATTGATCATA GGTATTTCAA AACACATCTT TCCTGTCTGC ACAAGTGAAG     150
TGTTTTGTTC TTTCTGGAGT CACAGTTGAC AAAAAGCTCT TACACTACAT     200
TAGAACACTG CATTAGAGCC CATTTCAATT CTCAAAAGAA AAGGCAAAAC     250
CTGGGATATC AATTAATTTG AAAACATAAT CTGCAAAGAA TGAGAAGGAG     300
TCAGAAACTG TTTCTGTAGC TTGTTCCCTG TCTTGTCCAT GTGGTTCTTC     350
AAATTTTGAT GCCAAGAAAG TATTTGGTAG GCCTAATGAA GGAGTTCACT     400
GTAAGACTCA TTCCCTAGAT CTTTCTATTC CAAAGTGCCA CTCATTCCTG     450
TAGTCAAAAT CTGGTCATGT TGGTCAAAAG CCTGGATTAT TTAGATCTAG     500
AAACAGATCT TGAAATCTGA ATGCTCTGGT TTGAGCAATT TTCGAACATT     550
CTTTGCCTGG TGCACTGTGT CTGTGGTGCC AGAGGCGTCC GTGGATCCAG     600
AGGTGGTTAT GACTCGTGCT GCATGCCTGG TCTTTCCTCT GTTTCTCCTT     650
CTGAAAGTTT TCTATACCTG TCTCCTTTCT CAGCCACAAA ATAAATGTTG     700
GGAGAAATGA TATATACCAC TTTCCCA                              727
```

( 2 ) INFORMATION FOR SEQ ID NO: 10:

( i ) SEQUENCE CHARACTERISTICS:
( A ) LENGTH: 27 base pairs
( B ) TYPE: nucleotide
( C ) STRANDEDNESS: single
( D ) TOPOLOGY: linear ( x i ) SEQUENCE DESCRIPTION: SEQ ID NO: 10:

```
CAGCCTGGTT AAGTCCAAGC TGAATTC                               27
```

( 2 ) INFORMATION FOR SEQ ID NO: 11:

( i ) SEQUENCE CHARACTERISTICS:
( A ) LENGTH: 22 base pairs
( B ) TYPE: nucleotide
( C ) STRANDEDNESS: single
( D ) TOPOLOGY: linear ( x i ) SEQUENCE DESCRIPTION: SEQ ID NO: 11:

```
CCTTCGAGAC CTTCTGGGGT GG                                    22
```

( 2 ) INFORMATION FOR SEQ ID NO: 12:

( i ) SEQUENCE CHARACTERISTICS:
( A ) LENGTH: 22 base pairs
( B ) TYPE: nucleotide
( C ) STRANDEDNESS: single
( D ) TOPOLOGY: linear ( x i ) SEQUENCE DESCRIPTION: SEQ ID NO: 12:

```
CTGTTCAGTG CACACCAAGC GC                                    22
```

( 2 ) INFORMATION FOR SEQ ID NO: 13:

( i ) SEQUENCE CHARACTERISTICS:
( A ) LENGTH: 27 base pairs
( B ) TYPE: nucleotide
( C ) STRANDEDNESS: single
( D ) TOPOLOGY: linear ( x i ) SEQUENCE DESCRIPTION: SEQ ID NO: 13:

CATGGAGCGA AGAGCCTGGA GTCTGCA 27

( 2 ) INFORMATION FOR SEQ ID NO: 14:

( i ) SEQUENCE CHARACTERISTICS:
( A ) LENGTH: 19 base pairs
( B ) TYPE: nucleotide
( C ) STRANDEDNESS: single
( D ) TOPOLOGY: linear ( x i ) SEQUENCE DESCRIPTION: SEQ ID NO: 14:

GACTCCAGGC TCTTCGCTC 19

( 2 ) INFORMATION FOR SEQ ID NO: 15:

( i ) SEQUENCE CHARACTERISTICS:
( A ) LENGTH: 29 base pairs
( B ) TYPE: nucleotide
( C ) STRANDEDNESS: single
( D ) TOPOLOGY: linear ( x i ) SEQUENCE DESCRIPTION: SEQ ID NO: 15:

GATCCACGCG TCCCGGGGG TACCATGGAT 29

( 2 ) INFORMATION FOR SEQ ID NO: 16:

( i ) SEQUENCE CHARACTERISTICS:
( A ) LENGTH: 27 bases
( B ) TYPE: nucleotide
( C ) STRANDEDNESS: single
( D ) TOPOLOGY: linear ( x i ) SEQUENCE DESCRIPTION: SEQ ID NO: 16:

CGATCCATGG TACCCCCGGG ACGCGTG 27

( 2 ) INFORMATION FOR SEQ ID NO: 17:

( i ) SEQUENCE CHARACTERISTICS:
( A ) LENGTH: 33 base pairs
( B ) TYPE: nucleotide
( C ) STRANDEDNESS: single
( D ) TOPOLOGY: linear ( x i ) SEQUENCE DESCRIPTION: SEQ ID NO: 17:

CAGGATCCAA AAGGCAATTT GTCAATGAAT GGG 33

( 2 ) INFORMATION FOR SEQ ID NO: 18:

( i ) SEQUENCE CHARACTERISTICS:
( A ) LENGTH: 32 base pairs
( B ) TYPE: nucleotide
( C ) STRANDEDNESS: single
( D ) TOPOLOGY: linear ( x i ) SEQUENCE DESCRIPTION: SEQ ID NO: 18:

TTGAATTCTT ATAGTGCTGA GTCCCTTAGA GC 32

( 2 ) INFORMATION FOR SEQ ID NO: 19:

( i ) SEQUENCE CHARACTERISTICS:
( A ) LENGTH: 29 base pairs
( B ) TYPE: nucleotide
( C ) STRANDEDNESS: single
( D ) TOPOLOGY: linear ( x i ) SEQUENCE DESCRIPTION: SEQ ID NO: 19:

GTGGATCCTC AGCTCTAAGG GACTCAGCA 29

( 2 ) INFORMATION FOR SEQ ID NO: 20:

( i ) SEQUENCE CHARACTERISTICS:
( A ) LENGTH: 32 base pairs
( B ) TYPE: nucleotide
( C ) STRANDEDNESS: single
( D ) TOPOLOGY: linear ( x i ) SEQUENCE DESCRIPTION: SEQ ID NO: 20:

TCGAATTCTT AGGAATATTC AATTGTTGCT TC 32

( 2 ) INFORMATION FOR SEQ ID NO: 21:

( i ) SEQUENCE CHARACTERISTICS:
( A ) LENGTH: 29 base pairs
( B ) TYPE: nucleotide
( C ) STRANDEDNESS: single
( D ) TOPOLOGY: linear ( x i ) SEQUENCE DESCRIPTION: SEQ ID NO: 21:

GTGGATCCGA TGAGTTGGAG GAGGGAGCC 29

( 2 ) INFORMATION FOR SEQ ID NO: 22:

( i ) SEQUENCE CHARACTERISTICS:
( A ) LENGTH: 29 base pairs
( B ) TYPE: nucleotide
( C ) STRANDEDNESS: single
( D ) TOPOLOGY: linear ( x i ) SEQUENCE DESCRIPTION: SEQ ID NO: 22:

CAGAATTCTT AATTTTCCTC ATTCAGAAT 29

( 2 ) INFORMATION FOR SEQ ID NO: 23:

( i ) SEQUENCE CHARACTERISTICS:
( A ) LENGTH: 26 base pairs
( B ) TYPE: nucleotide
( C ) STRANDEDNESS: single
( D ) TOPOLOGY: linear ( x i ) SEQUENCE DESCRIPTION: SEQ ID NO: 23:

CGGGATCCGA GAGACCCGTC TTCACG 26

( 2 ) INFORMATION FOR SEQ ID NO: 24:

( i ) SEQUENCE CHARACTERISTICS:
( A ) LENGTH: 32 base pairs
( B ) TYPE: nucleotide
( C ) STRANDEDNESS: single
( D ) TOPOLOGY: linear ( x i ) SEQUENCE DESCRIPTION: SEQ ID NO: 24:

CAGAATTCTT ACTCATTGAT GTCCCTGTAC CC 32

( 2 ) INFORMATION FOR SEQ ID NO: 25:

( i ) SEQUENCE CHARACTERISTICS:

( A ) LENGTH: 30 base pairs
( B ) TYPE: nucleotide
( C ) STRANDEDNESS: single
( D ) TOPOLOGY: linear ( x i ) SEQUENCE DESCRIPTION: SEQ ID NO: 25:

AACCCGGGAG GGTACAGGGA CATCAATGAG 30

( 2 ) INFORMATION FOR SEQ ID NO: 26:

( i ) SEQUENCE CHARACTERISTICS:
( A ) LENGTH: 32 base pairs
( B ) TYPE: nucleotide
( C ) STRANDEDNESS: single
( D ) TOPOLOGY: linear ( x i ) SEQUENCE DESCRIPTION: SEQ ID NO: 26:

CAGAATTCTT ACTCATTGAT GTCCCTGTAC CC 32

( 2 ) INFORMATION FOR SEQ ID NO: 27:

( i ) SEQUENCE CHARACTERISTICS:
( A ) LENGTH: 28 base pairs
( B ) TYPE: nucleotide
( C ) STRANDEDNESS: single
( D ) TOPOLOGY: linear ( x i ) SEQUENCE DESCRIPTION: SEQ ID NO: 27:

CGGAATTCTA GTTCTTTCTC AGGATACT 28

( 2 ) INFORMATION FOR SEQ ID NO: 28:

( i ) SEQUENCE CHARACTERISTICS:
( A ) LENGTH: 29 base pairs
( B ) TYPE: nucleotide
( C ) STRANDEDNESS: single
( D ) TOPOLOGY: linear ( x i ) SEQUENCE DESCRIPTION: SEQ ID NO: 28:

CCGGATCCGG CACCAAGTCC ATTTTGCTG 29